United States Patent
Fernandes

[11] Patent Number: 5,946,431
[45] Date of Patent: Aug. 31, 1999

[54] MULTI-FUNCTIONAL PHOTOMETER WITH MOVABLE LINKAGE FOR ROUTING LIGHT-TRANSMITTING PATHS USING REFLECTIVE SURFACES

[75] Inventor: Jorge Fernandes, Los Altos Hills, Calif.

[73] Assignee: Molecular Dynamics, Sunnyvale, Calif.

[21] Appl. No.: 08/900,087

[22] Filed: Jul. 24, 1997

Related U.S. Application Data

[60] Continuation-in-part of application No. 08/373,408, Jan. 17, 1995, Pat. No. 5,542,012, which is a division of application No. 08/100,541, Jul. 30, 1993, Pat. No. 5,436,718.

[51] Int. Cl.$^6$ .............................. G02B 6/24; G01N 21/59; G01N 21/64
[52] U.S. Cl. .............................. 385/25; 385/15; 385/24; 356/73; 356/318; 356/417; 356/418; 356/440; 250/458.1
[58] Field of Search .................... 385/15, 16, 22, 385/24, 25, 18, 19, 20, 21, 59, 31, 33; 356/73, 318, 417, 418, 436, 440; 250/227.23, 227.26, 458.1, 459.1, 461.1, 462.2

[56] References Cited

U.S. PATENT DOCUMENTS

| | | | |
|---|---|---|---|
| Re. 34,605 | 5/1994 | Schrenk et al. | 359/359 |
| 1,610,423 | 12/1926 | Cawley | 353/20 |

(List continued on next page.)

FOREIGN PATENT DOCUMENTS

| | | | |
|---|---|---|---|
| 1327286 | 3/1994 | Canada | 88/113.18 |
| 218041 | 12/1993 | China | G02F 1/1335 |
| 062751 | 10/1981 | European Pat. Off. | G02B 1/08 |
| 0062160 | 3/1982 | European Pat. Off. | 385/12 X |
| 056843 | 8/1982 | European Pat. Off. | G02F 1/33 |
| 0314507 | 5/1989 | European Pat. Off. | H05B 33/20 |
| 469732 | 2/1992 | European Pat. Off. | G92B 1/04 |
| 0516274 | 4/1992 | European Pat. Off. | 385/15 X |
| 514223 | 11/1992 | European Pat. Off. | G02B 5/08 |
| 0583066 | 7/1993 | European Pat. Off. | 385/25 X |
| 552725 | 7/1993 | European Pat. Off. | G02B 27/28 |
| 573905 | 12/1993 | European Pat. Off. | G02B 27/28 |
| 597261 | 5/1994 | European Pat. Off. | G02F 1/1335 |
| 606939 | 7/1994 | European Pat. Off. | G02F 1/1335 |
| 606940 | 7/1994 | European Pat. Off. | G02B 5/30 |
| 4121861 | 1/1992 | Germany | G02B 5/30 |
| 63-181201 | 7/1988 | Japan | F21V 5/02 |
| 4-141603 | 5/1992 | Japan | G02B 5/30 |
| 4-184429 | 7/1992 | Japan | G03B 21/14 |
| 5-288910 | 11/1993 | Japan | G02B 5/18 |
| 6-11607 | 1/1994 | Japan | G02B 5/18 |
| 2052779 | 1/1981 | United Kingdom | G02F 1/133 |
| 9210737 | 12/1990 | WIPO | 385/25 X |

(List continued on next page.)

OTHER PUBLICATIONS

Video Tape Entitled, "The Cytofluor Fluorescence Measurement System—Automated Fluorescence Scanning", Millipore, 1990, (previously submitted in parent file).

(List continued on next page.)

*Primary Examiner*—Brian Healy
*Attorney, Agent, or Firm*—Blakely, Sokoloff, Taylor & Zafman

[57] ABSTRACT

A multi-functional photometer includes a scanning mechanism having a housing that bears a movable linkage. The linkage is coupled to an optical scanning head and incorporates light-transmitting paths with at least one reflective surface for transmitting radiant energy to and from the scanning head. The arm comprises a C-shaped elbow member, pivotally attached to a shoulder member. In turn, the shoulder member of the arm is pivotally connected to the housing. In one embodiment the reflective surfaces are optically coupled and are mounted onto the housing, shoulder member and elbow member, such that the shapes of the light-transmitting paths remain fixed regardless of the orientation of the arm. The housing further incorporates a Cartesian-coordinate table for positioning the scanning head with respect to a microplate that contains a plurality of analyte samples.

41 Claims, 13 Drawing Sheets

U.S. PATENT DOCUMENTS

| | | | |
|---|---|---|---|
| 2,492,809 | 12/1949 | Marks | 88/65 |
| 2,887,566 | 5/1959 | Marks | 240/9.5 |
| 3,213,753 | 10/1965 | Rogers | 88/65 |
| 3,528,723 | 9/1970 | Rogers | 359/359 X |
| 3,610,729 | 10/1971 | Rogers | 359/359 X |
| 3,647,612 | 3/1972 | Schrenk et al. | 161/165 |
| 3,697,185 | 10/1972 | Kassel et al. | 356/181 |
| 3,711,176 | 1/1973 | Alfrey, Jr. et al. | 350/1 |
| 3,759,647 | 9/1973 | Schrenk et al. | 425/131 |
| 3,773,882 | 11/1973 | Schrenk | 264/171 |
| 3,801,429 | 4/1974 | Schrenk et al. | 161/181 |
| 3,847,585 | 11/1974 | Chisholm | 65/99 |
| 3,874,780 | 4/1975 | Love | 385/15 X |
| 3,935,351 | 1/1976 | Franz | 428/34 |
| 3,949,134 | 4/1976 | Wildorf | 428/215 |
| 3,990,784 | 11/1976 | Gelber | 350/166 |
| 4,025,688 | 5/1977 | Nagy et al. | 428/350 |
| 4,069,630 | 1/1978 | Chess et al. | 52/172 |
| 4,076,889 | 2/1978 | Sasaki et al. | 428/333 |
| 4,094,947 | 6/1978 | Alfrey, Jr. et al. | 264/171 |
| 4,095,013 | 6/1978 | Burger | 428/522 |
| 4,158,718 | 6/1979 | Kehl et al. | 428/461 |
| 4,223,978 | 9/1980 | Kummer et al. | 385/22 X |
| 4,268,127 | 5/1981 | Oshima et al. | 350/337 |
| 4,303,302 | 12/1981 | Ramsey et al. | 385/22 X |
| 4,308,316 | 12/1981 | Gordon | 428/336 |
| 4,310,584 | 1/1982 | Cooper et al. | 428/212 |
| 4,315,258 | 2/1982 | McKnight et al. | 340/784 |
| 4,373,779 | 2/1983 | Dorsey | 385/25 X |
| 4,415,229 | 11/1983 | McCullough | 385/22 X |
| 4,427,741 | 1/1984 | Aizawa et al. | 428/332 |
| 4,446,305 | 5/1984 | Rogers et al. | 528/348 |
| 4,477,190 | 10/1984 | Liston et al. | 356/418 |
| 4,500,173 | 2/1985 | Leibowitz et al. | 359/359 X |
| 4,501,970 | 2/1985 | Nelson | 250/458.1 |
| 4,513,023 | 4/1985 | Wary | 427/54.1 |
| 4,520,189 | 5/1985 | Rogers et al. | 528/331 |
| 4,521,588 | 6/1985 | Rogers et al. | 528/363 |
| 4,525,413 | 6/1985 | Rogers et al. | 428/212 |
| 4,534,743 | 8/1985 | D'Onofrio et al. | 445/24 |
| 4,540,623 | 9/1985 | Im et al. | 428/220 |
| 4,587,812 | 5/1986 | Brega | 66/232 |
| 4,622,468 | 11/1986 | Stefanski et al. | 250/458.1 |
| 4,626,684 | 12/1986 | Landa | 250/328 |
| 4,669,878 | 6/1987 | Meier | 356/319 |
| 4,678,285 | 7/1987 | Ohta et al. | 359/359 X |
| 4,730,922 | 3/1988 | Bach et al. | 356/73 |
| 4,750,837 | 6/1988 | Gifford et al. | 356/417 |
| 4,798,448 | 1/1989 | van Raalte | 359/359 X |
| 4,799,756 | 1/1989 | Hirschfeld | 385/33 X |
| 4,802,768 | 2/1989 | Gifford et al. | 356/417 |
| 4,815,812 | 3/1989 | Miller | 385/25 X |
| 4,820,045 | 4/1989 | Boisde et al. | 356/319 |
| 4,840,485 | 6/1989 | Gratton | 356/317 |
| 4,896,935 | 1/1990 | Lee | 385/22 X |
| 4,917,465 | 4/1990 | Conner et al. | 359/359 X |
| 4,937,134 | 6/1990 | Schrenk et al. | 428/213 |
| 4,937,457 | 6/1990 | Mitchell | 250/458.1 |
| 4,945,245 | 7/1990 | Levin | 250/461.2 |
| 4,968,148 | 11/1990 | Chow et al. | 356/427 |
| 4,971,843 | 11/1990 | Michelotti et al. | 428/34 |
| 5,030,832 | 7/1991 | Williams et al. | 250/458.1 |
| 5,089,318 | 2/1992 | Shetty et al. | 428/212 |
| 5,094,788 | 3/1992 | Schrenk et al. | 264/171 |
| 5,094,793 | 3/1992 | Schrenk et al. | 264/171 |
| 5,095,210 | 3/1992 | Wheatley et al. | 250/339 |
| 5,103,337 | 4/1992 | Schrenk et al. | 359/359 |
| 5,122,905 | 6/1992 | Wheatley et al. | 359/386 |
| 5,122,906 | 6/1992 | Wheatley | 359/586 |
| 5,125,747 | 6/1992 | Sayegh et al. | 356/407 |
| 5,126,880 | 6/1992 | Wheatley et al. | 359/587 |
| 5,131,746 | 7/1992 | O'Rourke et al. | 356/319 |
| 5,141,609 | 8/1992 | Sweedler et al. | 204/180.1 |
| 5,143,853 | 9/1992 | Walt | 436/501 |
| 5,149,578 | 9/1992 | Wheatley et al. | 428/213 |
| 5,151,869 | 9/1992 | Alcala | 364/497 |
| 5,157,526 | 10/1992 | Kondo et al. | 359/63 |
| 5,159,478 | 10/1992 | Akiyama et al. | 359/69 |
| 5,202,074 | 4/1993 | Schrenk et al. | 264/241 |
| 5,214,727 | 5/1993 | Carr et al. | 385/22 |
| 5,217,794 | 6/1993 | Schrenk | 428/220 |
| 5,233,465 | 8/1993 | Wheatley et al. | 359/359 |
| 5,234,729 | 8/1993 | Wheatley et al. | 428/30 |
| 5,255,029 | 10/1993 | Vogeley et al. | 353/122 |
| 5,269,995 | 12/1993 | Ramanathan et al. | 264/171 |
| 5,278,694 | 1/1994 | Wheatley et al. | 359/359 |
| 5,316,703 | 5/1994 | Schrenk | 264/1.3 |
| 5,325,218 | 6/1994 | Willett et al. | 359/53 |
| 5,333,072 | 7/1994 | Willett | 359/41 |
| 5,339,198 | 8/1994 | Wheatley et al. | 359/359 |
| 5,353,363 | 10/1994 | Keck et al. | 385/25 X |
| 5,360,659 | 11/1994 | Arends et al. | 428/216 |
| 5,389,324 | 2/1995 | Lewis et al. | 264/171 |
| 5,422,756 | 6/1995 | Weber | 359/487 |
| 5,424,119 | 6/1995 | Phillips et al. | 428/328 |
| 5,436,718 | 7/1995 | Fernandes et al. | 356/73 |
| 5,448,404 | 9/1995 | Schrenk et al. | 359/584 |
| 5,451,449 | 9/1995 | Shetty et al. | 428/195 |
| 5,486,949 | 1/1996 | Schrenk et al. | 359/498 |
| 5,540,978 | 7/1996 | Schrenk | 428/212 |
| 5,542,012 | 7/1996 | Fernandes | 385/25 |
| 5,552,927 | 9/1996 | Wheatley et al. | 359/101 |
| 5,568,316 | 10/1996 | Schrenk et al. | 359/584 |

FOREIGN PATENT DOCUMENTS

| | | | |
|---|---|---|---|
| WO 91/09719 | 7/1991 | WIPO | B32B 5/30 |
| WO 94/11776 | 5/1994 | WIPO | G02F 1/1335 |
| WO 94/29765 | 12/1994 | WIPO | B29C 59/04 |
| WO 95/17303 | 6/1995 | WIPO | B32B 7/02 |
| WO 95/17691 | 6/1995 | WIPO | G02B 5/30 |
| WO 95/17692 | 6/1995 | WIPO | G02B 5/30 |
| WO 95/17699 | 6/1995 | WIPO | G02F 1/1335 |

OTHER PUBLICATIONS

PCT International Search Report for International Application No. PCT/US/94/06894, Mailed Aug. 25, 1994.

PCT International Written Opinion for International Application No. PCT/US/94/06894, Mailed Mar. 14, 1995.

Supplementary European Search Report, Jul. 15, 1997.

E. Karjalainen, et al., "A Multichannel Photometer for Chemical Analysis", Journal of Physics E. Scientific Instruments, vol. 7, No. 4, Apr. 1974, Bristol GB, pp. 241–243.

Lin, F., "A1,4: :Non–Imaging CCFT Coupler for LCD Backlighting", *SID 94 Digest*, vol. XXV, pp. 14–15 (1994).

Schrenk, W. et al., "Coextruded Elastomeric Optical Interference Film", SPE Annual Technical Conference, Atlanta, GA pp. 1703–1707 (1988).

Schrenk, W. et al., "Coextruded Infrared Reflecting Films", 7th Annual Meeting Polymer Processing Society, Hamilton, Ontario, Canada, pp. 222–223 (Apr. 1991).

Schrenk et al., "Coextruded Iridescent Film", TAPPI 1976 Paper Synthetics Conf., Atlanta, GA, pp. 141–145 (Sep. 27–29, 1976).

Im, J. et al., "Coextruded Microlayer Film and Sheet", *Journal of Plastic Film and Sheeting*, vol. 4, pp. 104–115 (Apr. 1988).

Schrenk et al., "Coextruded Multilayer Polymer Films and Sheet", *Polymer Blends,* vol. 2, Ch. 15, pp. 129–165, Academic Press, Inc. (1978).

Hodgkinson, I. et al., "Effective Principal Refractive Indices and Column Angles for Periodic Stacks of Thin Birefringent Films", *J. Opt. Soc. Am. A,* vol. 10, No. 9, pp. 2065–2071 (1993).

Wu et al., "High Transparent Sheet Polarizer Made with Birefringent Materials", *Jpn. J. of App. Phys.,* vol. 34, pp. L 997–999 (Aug. 1995).

Schrenk et al., "Interfacial Flow Instability in Multilayer Coextrusion", *Polymer Engineering and Science,* vol. 18 (8), pp. 620–623 (Jun. 1978).

Schrenk, W., "New Developments in Coextrusion", International Conference on Advances In Polymer Processing, New Orleans, Louisiana, (Apr., 1991).

Alfrey, Jr. et al., "Physical Optics of Iridescent Multilayered Plastic Films", *Polymer Engineering and Science, ,* vol. 9, No. 6, pp. 400–404 (Nov. 1969).

Radford et al., "Reflectivity of Iridescent Coextruded Multilayered Plastic Films", "Reflectivity of Iridescent Coextruded Multilayered Plastic Films", *Polymer Engineering and Science,* vol. 13, No. 3, (May 1973); Dow Chemical Co., American Chemical Society Symposium on "Coextruded Plastic Films, Fibers, Composites", Apr. 9–14, 1972.

Weber, M., "23:3: Retroreflecting Sheet Polarizer", *SID 92 Digest,* pp. 427–429 (1992).

Weber, M., "P–61: Retroreflecting Sheet Polarizer", *SID 93 Digest,* pp. 669–672 (1993).-

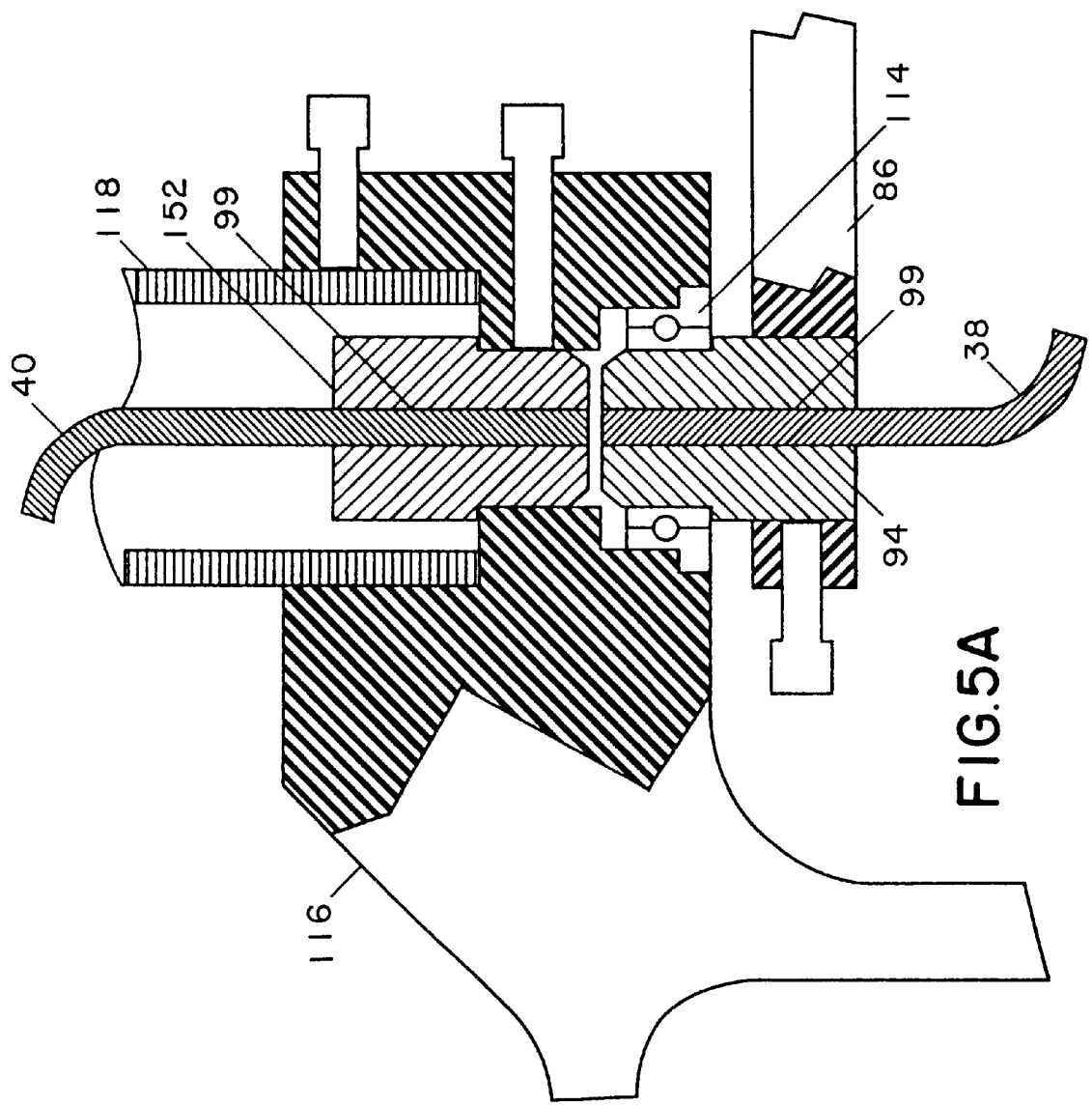

MULTI-FUNCTIONAL PHOTOMETER WITH MOVABLE LINKAGE FOR ROUTING LIGHT-TRANSMITTING PATHS USING REFLECTIVE SURFACES

CROSS-REFERENCE TO RELATED APPLICATIONS

This is a continuation-in-part of our application entitled "MULTI-FUNCTIONAL PHOTOMETER WITH MOVABLE LINKAGE FOR ROUTING OPTICAL FIBERS", Ser. No. 08/373,408, filed Jan. 17, 1995, now U.S. Pat. No. 5,542,012, which is a divisional application of application entitled: "MULTI-FUNCTIONAL PHOTOMETER WITH MOVABLE LINKAGE FOR ROUTING OPTICAL FIBERS," Ser. No. 08/100,541, filed Jul. 30, 1993, now U.S. Pat. No. 5,436,718, and assigned to the instant assignee.

FIELD OF THE INVENTION

The present invention relates to the field of spectroscopy, particularly to a multi-functional photometer capable of measuring light absorbance, fluorescence, and luminescence of a sample.

BACKGROUND OF THE INVENTION

In biological research, it is often necessary to assay samples for content of various chemicals, hormones, and enzymes. Spectroscopy, which is the measurement and interpretation of electromagnetic radiation absorbed or emitted when the molecules, or atoms, of a sample move from one energy state to another, is widely utilized for this purpose. Currently, the most common spectroscopic techniques pertain to measurements of absorbance, fluorescence, and luminescence.

Chemical analyses with absorption spectroscopy allow one to determine concentrations of specific components, to assay chemical reactions, and to identify individual compounds. Absorbance measurements are most commonly used to find the concentration of a specific composition in a sample. According to Beer's law, for a composition that absorbs light at a given wavelength, the total absorbed quantity of such light is related to the quantity of that composition in the sample.

Fluorescence, in turn, is a physical phenomenon based upon the ability of some substances to absorb and subsequently emit electromagnetic radiation. The emitted radiation has a lower energy level and a longer wavelength than the excitation radiation. Moreover, the absorption of light is wavelength dependent. In other words, a fluorescent substance emits light only when the excitation radiation is in the particular excitation band (or bands) of that substance.

For fluorescence measurements, fluorescent dyes called fluorophores are often used to "tag" molecules of interest, or targets. After being irradiated by an excitation beam, fluorophores, bonded to the targets, emit light that is then collected and quantized. The ratio of the intensity of the emitted fluorescent light to the intensity of the excitation light is called the "relative fluorescence intensity" and serves as an indicator of target concentration. Another useful characteristic is the phase relationship between the cyclic variations in the emitted light and the variations in the excitation light, i.e., the time lag between corresponding variations in the emission and excitation beams.

As noted above, luminescence measurements can also be employed for analyzing biological samples. Luminescence is the property of certain chemical substances to emit light as a result of a chemical change; no excitation from a light source is necessary. Moreover, luminescence can be produced by energy-transfer mechanisms that take energy of a high intensity, e.g., a radioactive emission, and transform it to energy of a low intensity, e.g., a flash of light At the present time, a variety of spectroscopic instruments are commonly used in the art. A number of these instruments are designed to be utilized in conjunction with multi-site analyte receptacles called "microplates", which usually comprise one-piece structures having multiplicities of wells for holding analyte samples. Microplates are beneficial since they allow simultaneous preparation of a large number of test samples. Moreover, microplates are inexpensive, safe, sturdy, and convenient to handle. They are also disposable and can be cleaned easily when necessary.

One instrument currently available for fluorescent analysis of samples in microplate wells is the Cytofluor 2300 fluorometer, distributed by Millipore Corporation, Bedford, Mass. This fluorometer includes a scanning head that resides underneath the microplate and moves along the bottom face thereof to scan the sample sites. The scanning head interfaces with the optical system of the device via a bundle of optical fibers that transmits excitation and emission radiation.

However, the capabilities of the Cytofluor 2300 fluorometer are limited in that it cannot perform absorbance measurements. Furthermore, the movement of the scanning head from one microplate well to another continuously alters the geometrical configuration of the optical-fiber bundle that is attached to the head. Consequently, curvatures of the light-transmitting fibers change, introducing variations in their optical properties. These variations create inconsistencies in readings between different wells and adversely affect the repeatability, and thus, accuracy of measurements. Moreover, continuous bending of the fibers produces stresses that cause mechanical failure of the fiber cores.

Additionally, to allow unrestricted movement of the scanning head, flexible plastic fibers are employed, as opposed to less pliable quartz fibers. On the down side, plastic fibers cannot efficiently transmit radiant energy in the ultraviolet (UV) region of the spectrum. Accordingly, the fluorometer is unable to perform measurements, such as binding studies of certain proteins, e.g., tryptophan, since fluorescence analyses of this type require the use of UV radiation. Furthermore, the deformation resistance of the optical-fiber bundle slows the movements of the scanning head, thus limiting the ability of the apparatus to perform kinetic measurements.

Another spectroscopic apparatus utilizing microplates is disclosed in U.S. Pat. No. 4,968,148 to Chow et al., 1990. Chow's device uses an optical distributing element to selectively direct radiant energy to specified microplate sites. One drawback of this instrument is its inability to perform fluorescence measurements. Moreover, the large number of fibers unnecessarily complicates the apparatus and increases production costs. Also, the light-delivery system of the instrument has a fixed geometry that can only accommodate a microplate with one particular well layout. Chow's apparatus does not have the versatility to be utilized with microplates having different configurations of wells.

OBJECTS AND SUMMARY OF THE INVENTION

It is accordingly an object of the invention to provide a multi-functional photometer which overcomes the foregoing disadvantages, e.g., which measures absorbance, fluorescence, and luminescence of a sample; which provides repeatable measurements and produces consistent readings between different test sites; which eliminates recurring bending of optical fibers and mechanical failure thereof; which utilizes optical radiation ranging from the ultraviolet to the infrared spectrum; which is able to carry out kinetic measurements; which can accommodate microplates with different well configurations; and which is relatively simple and inexpensive to manufacture.

Another object of the invention is to supply a photometer having a movable linkage for dynamically and interconnectingly routing optical fibers such that a constant configuration thereof is always maintained during operation of the photometer.

Yet another object of the invention is to provide a photometer which performs analyses of optical signals resulting from phenomena of absorbance, fluorescence, and luminescence over a range of spectral wavelengths. Further objects and advantages will become apparent after consideration of the ensuing description and the accompanying drawings.

In the preferred embodiment of the present invention, a multi-functional photometer includes a scanning mechanism having a housing that bears an articulated movable arm. The arm is coupled to an optical scanning head and incorporates light-transmitting paths, which utilize reflective surfaces for transmitting radiant energy to and from the scanning head. The arm comprises a C-shaped "elbow" member, pivotally attached to a "shoulder" member. In turn, the "shoulder" member of the arm is pivotally connected to the housing. Dynamic couplings optically interconnect the reflective surfaces such that the light-transmitting paths remain fixed regardless of the orientation of the arm.

The housing further incorporates a Cartesian-coordinate table for positioning the scanning head with respect to a microplate that contains analyte samples. To measure absorbance, fluorescence, and luminescence of the samples, an optical system, incorporating a plurality of lenses, filters, and sensors is utilized. Radiant energy for these measurements is provided by a light source having a microcomputer-controlled power supply. The same microcomputer governs the operation of the optical system and the positioning table.

DESCRIPTION OF THE DRAWINGS

The present invention is illustrated by way of example, and not by way of limitation, in the figures of the accompanying drawings, where:

FIG. 5A is a sectional view of an optical-fiber coupling provided by the couplers such as the one shown in FIG. 5.

For purposes of illustration, these figures are not necessarily drawn to scale. In all of the figures, like components are designated by like reference numerals.

DETAILED DESCRIPTION

Throughout the following description, specific details, such as materials, dimensions, etc., are set forth in order to provide a more thorough understanding of the invention. However, the invention may be practiced without these particulars. In other instances, well known elements have not been shown or described to avoid unnecessarily obscuring the present invention. Accordingly, the specification and drawings are to be regarded in an illustrative, rather than a restrictive, sense.

Figure 1:
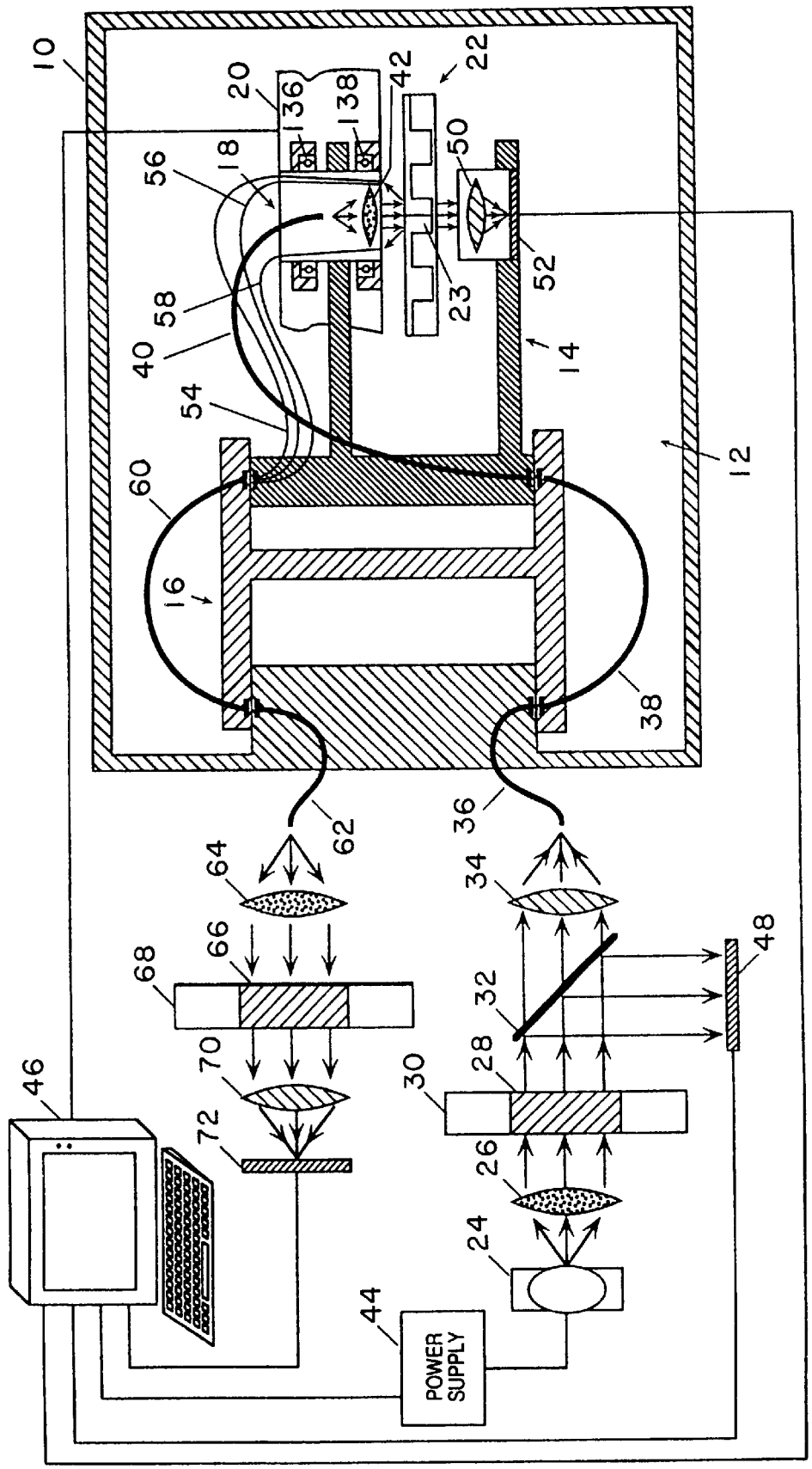
FIG. 1 is a schematic side view of a multi-functional photometer according to the present invention.

FIG. 1 shows a schematic side view of a multi-functional photometer according to the present invention. The photometer comprises a housing 10 that pivotally supports a movable arm 12, containing a C-shaped rigid "elbow" member 14 and a rigid "shoulder" member 16. The housing is approximately 21 cm tall, 18 cm wide, and 26 cm long. Arm 12 incorporates a plurality of optical fibers and is coupled to a first scanning element, e.g., an optical scanning head 18. The structure of arm 12 and the coupling mechanism of the optical fibers will be described fully in the ensuing section of the specification.

Scanning head 18 is rotationally attached through bearings 136 and 138 to a conventional positioning table 20, e.g., the Pen Plotter table, manufactured by Hewlett Packard Company of Palo Alto, Calif. Positioning tables like the Pen Plotter are often computer controlled such that the computer specifies X and Y coordinates of a point to be located by the mechanism of the table. Table 20 positions head 18 with respect to a microplate 22 that holds samples to be analyzed in a multiplicity of analyte wells, such as a well 23. As illustrated in FIG. 1, both table 20 and microplate 22 are supported within housing 10.

Figure 2:
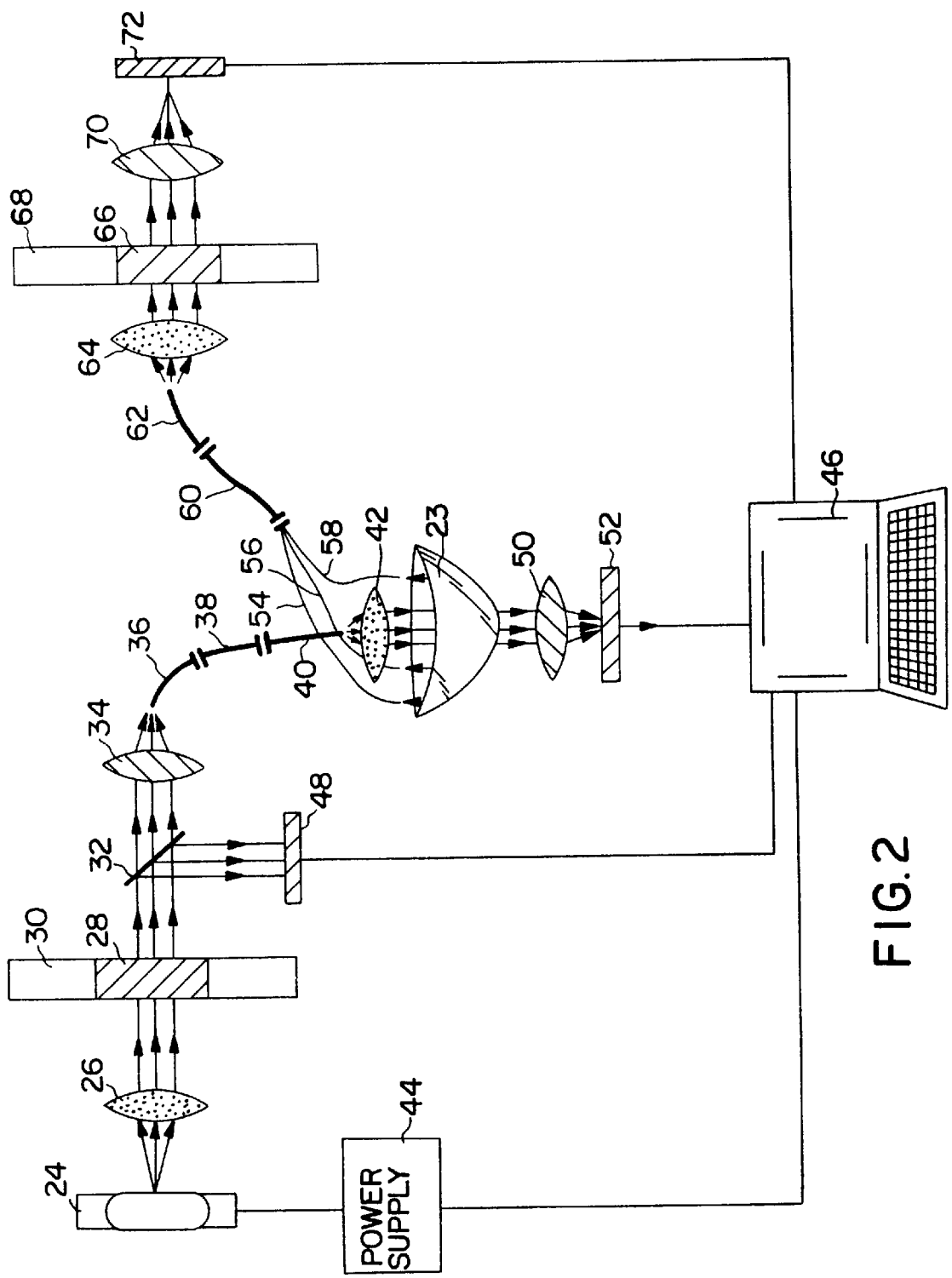
FIG. 2 is a schematic representation of an optical system utilized by the photometer of FIG. 1.

The optical system of the apparatus, described in reference to FIGS. 1 and 2, has a light-delivering assembly, a light-gathering assembly for absorbance measurements, and a light-gathering assembly for fluorescence and luminescence measurements. The light-delivering assembly includes a light source 24; a collimating lens 26; a plurality of bandpass filters 28, individually selectable by means of a rotary filter wheel 30; a beam splitter 32; a focusing lens 34; optical fibers 36, 38, and 40 arranged in series; and a collimating lens 42. Light source 24 typically comprises a xenon arc lamp, energized by a DC power supply 44, e.g., of Type 5 manufactured by Mimir Corporation of Sunnyvale, Calif. The power supply is controlled by a microcomputer 46, which also governs the positioning operations of table 20 and the functions of the optical system, e.g., the angular position of filter wheel 30. Microcomputer 46 may have, for example, a 80286 microprocessor from Intel Corporation of Santa Clara, Calif.

The light-gathering assembly for absorbance measurements comprises a reference-signal photodetector 48, a focusing lens 50, and a second scanning element for collecting light transmitted through microplate 22, e.g., a photodetector 52. Photodetectors 48 and 52, which convert electromagnetic radiation into electric current, may be implemented as photovoltaic cells. After being converted to a digital format by an analog-to-digital converter (not shown), the outputs of photodetectors 48 and 52 are analyzed by microcomputer 46.

The light-gathering assembly for fluorescence and luminescence measurements includes optical pick-up fibers 54, 56, and 58, arranged side-by-side. The pick-up fibers are collectively coupled to a light-transmitting fiber 60, which interfaces with an optical fiber 62. Upon exiting fiber 62, light passes through a collimating lens 64; one of a plurality of bandpass filters 66, selectable by turning a rotary filter wheel 68, which is computer-controlled; and a focusing lens 70. Lens 70 focuses the optical signal on a photodetector 72, whose output is then digitized and processed by microcomputer 46.

In an alternative embodiment of the optical system (FIG. 3), a light-dispersing device 74 replaces filter wheel 68 for fluorescence and luminescence measurements. Moreover, instead of being directed to photodetector 52, the optical signal, transmitted through one of a multiplicity of microplate wells 23, is channeled to the light-dispersing device through lens 50 via sequentially coupled optical fibers 76, 78, and 80. Light-dispersing device 74 comprises a diffraction grating that disperses incoming optical radiation into component wavelengths, which are gathered at photodetector 72. Thus, analyses of optical signals resulting from phenomena of absorbance, fluorescence, and luminescence can be performed over a range of wavelengths, rather than at a narrow spectral bandwidth provided by an individual filter. Consequently, valuable additional information may be learned about the properties of analyte samples being studied.

MOVABLE ARM FOR ROUTING OPTICAL FIBERS

Figure 4:
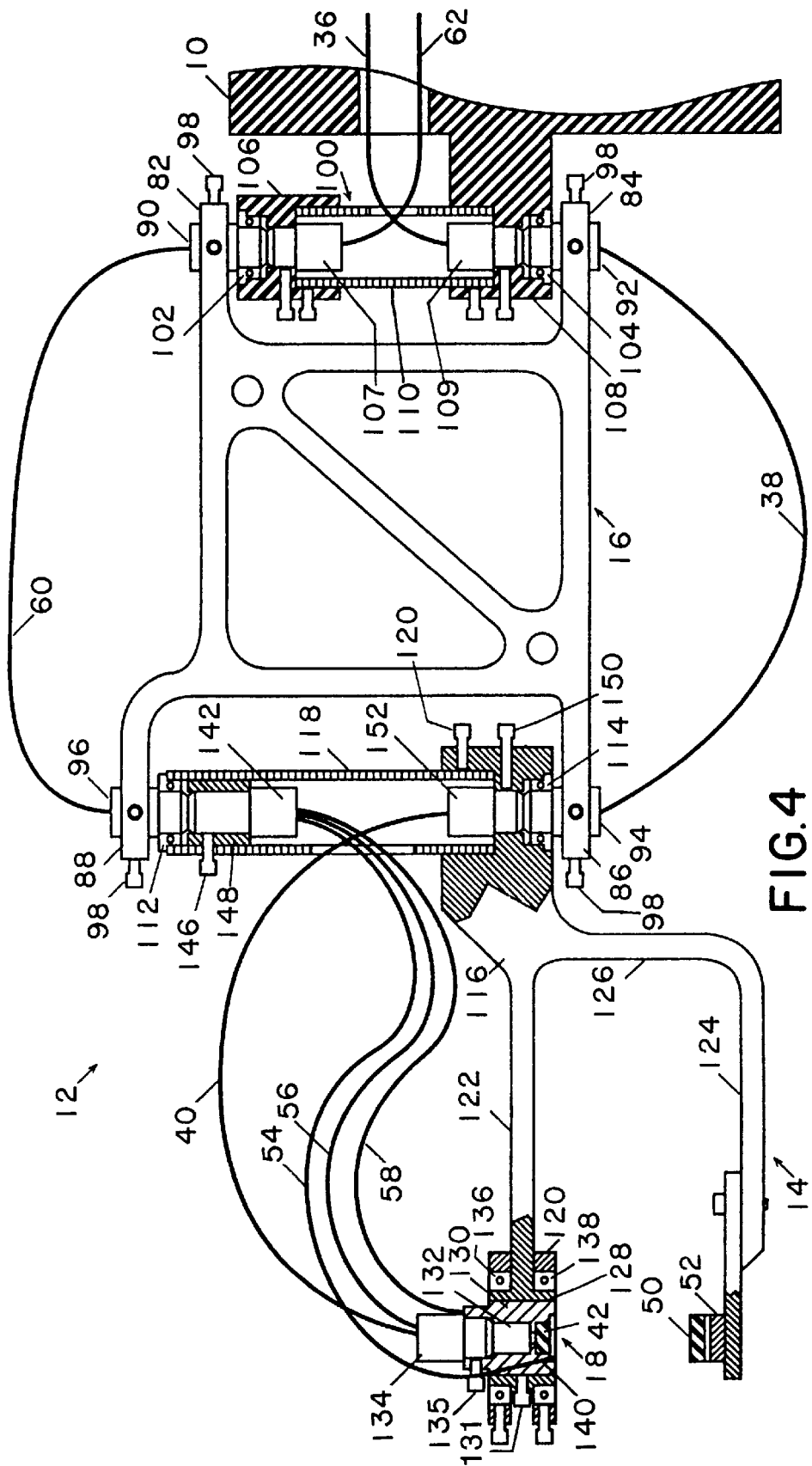
FIG. 4 is a side elevational view of a movable arm of the photometer illustrated in FIG. 1.

Movable arm 12, generally illustrated in FIG. 1, is shown in greater detail in FIG. 4. The arm comprises an articulated linkage having movably coupled members 14 and 16. Member 16 is a substantially rectangular structure having mounting protrusions 82, 84, 86, and 88. The protrusions contain openings accommodating optical-fiber couplers 90, 92, 94, and 96, respectively. The couplers are fixed inside the openings with threaded fasteners, e.g., set screws 98.

Figure 5:
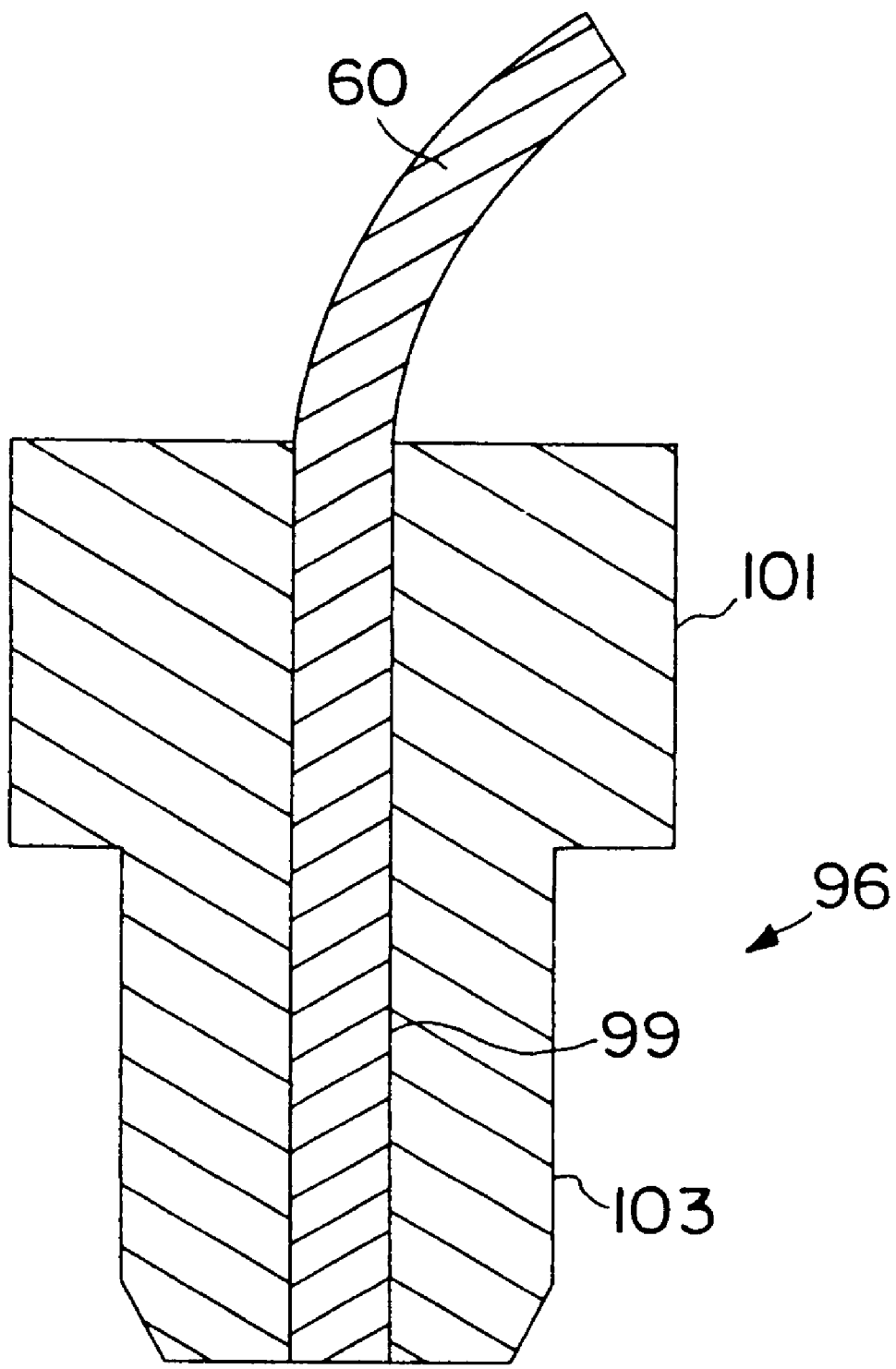
FIG. 5 is a sectional view of an optical-fiber coupler of the photometer of FIG. 1

As shown in FIG. 5, each of the couplers of the type described above, for example coupler 96, contains a centrally-disposed through bore 99, having a radial dimension that is uniform along the entire length of the bore. Moreover, each coupler has two distinct cylindrical surfaces 101 and 103. Surface 101 has a larger radial dimension then surface 103 and defines the end of the coupler where an optical fiber is to be inserted.

FIG. 4 further illustrates the pivotal attachment of member 16 to housing 10 by means of a bearing assembly 100, which includes a pair of ring bearings 102 and 104 that support couplers 90 and 92. Bearings 102 and 104 are retained within collars 106 and 108, respectively, where collar 108 is integral with housing 10. The two collars are rigidly interconnected by a hollow cylindrical sleeve 110. The above-described structure allows member 16 to pivot with respect to housing 10 about an axis defined by the vertical symmetry aids of sleeve 110.

Similarly, bearings 112 and 114 allow member 16 to pivotally support C-shaped member 14. The C-shaped member has a hinge portion 116, which is rigidly attached to one end of a cylindrical hollow sleeve 118 with a set screw 120. The inner races of bearings 112 and 114 are mounted on couplers 96 and 94, respectively. The outer race of bearing 114 sustains portion 116, while bearing 112 is inserted into the second end of sleeve 118. This structure permits member 14 to pivot with respect to member 16 about an axis defined by the vertical symmetry axis of sleeve 18.

Member 14 further includes parallel beams 122 and 124, integrally connected by a shank 126. Beam 122 contains a cylindrical bore 128 that accommodates scanning head 18 (first scanning element) whereas beam 124 bears the second scanning element comprising lens 50 and photodetector 52. The second scanning element, which is collinear with the scanning head, is located with respect to beam 124 with dowel pins (not shown) and is attached to the beam with screw-type fasteners.

Head 18 comprises a substantially cylindrical casing 130 that is retained inside bore 128, e.g., with a set screw 131. Casing 130 has a through longitudinal opening 132 that houses an optical-fiber coupler 134 at one end and lens 42 at the other. A set screw 135 anchors coupler 134 within opening 132. Ring bearings 136 and 138 are mounted on flanges defining bore 128 for rotationally coupling head 18 to positioning table 20 (schematically shown in FIG. 1). Casing 130 further comprises three through cavities 140 (only one of which is shown in FIG. 4), symmetrically arranged around opening 132 and having an angle of approximately 12° with respect to the vertical axis of the casing.

Cavities 140 contain ends of optical fibers 54, 56, and 58, which may be used to pick up fluorescent emissions. Due to the oblique arrangement of cavities 140, these fibers are less likely to receive excitation from fiber 40. The opposite ends of fibers 54, 56, and 58 are routed via a lateral opening in sleeve 118 into an optical-fiber integrator 142, which contains a through central opening for housing the fibers. Integrator 142 is anchored by a set screw 146 inside a through central bore of spacer 148, the latter being fixed by the same screw within sleeve 118. The integrator is positioned such that its central opening is collinear with the central bore of coupler 96 to allow exchange of radiant energy between fiber 60 and fibers 54, 56, and 56.

A set screw 150 secures an optical-fiber coupler 152, identical to couplers 90, 92, 94, 96, and 134, within a through opening in hinge portion 116 such that the bores of couplers 94 and 152 are collinear. The above-described couplers may be made of an opaque material, such as aluminum. Each coupler is about 6.1 mm long and the radial dimension of the longitudinal central bore is approximately 0.5 mm. The optical fibers inserted inside the couplers, e.g., couplers 94 and 152, completely occupy central bores 99 such that the ends of the fibers are flush with the end-faces of the couplers, as shown in FIG. 5A. The fibers are typically retained inside the couplers by friction or with an adhesive placed along the fiber shafts such that during insertion of the fibers into the couplers the end-faces of the fibers are not covered with the adhesive.

Figure 6:
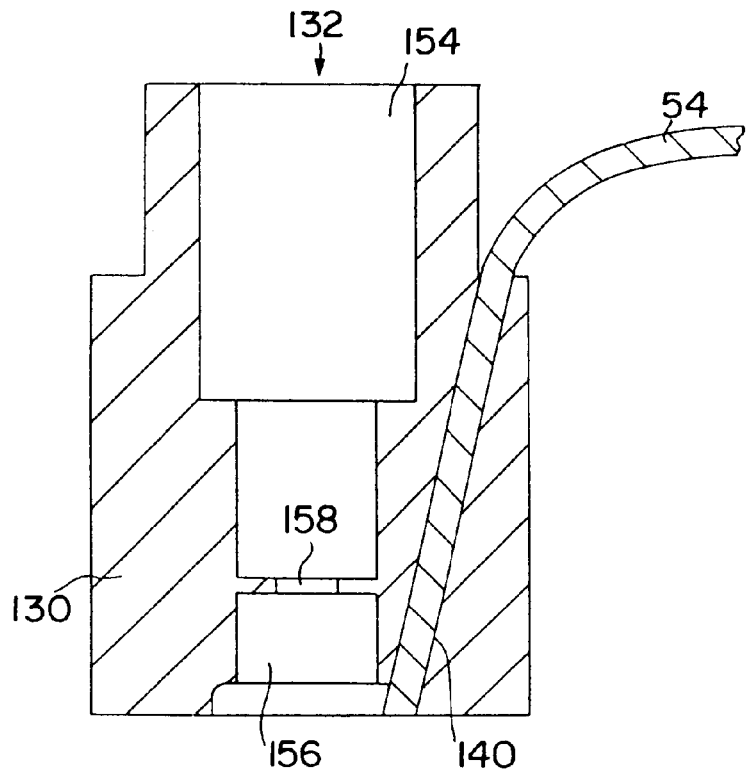
FIG. 6 is a sectional view of an optical scanning head of the photometer shown in FIG. 1.
Figure 7:
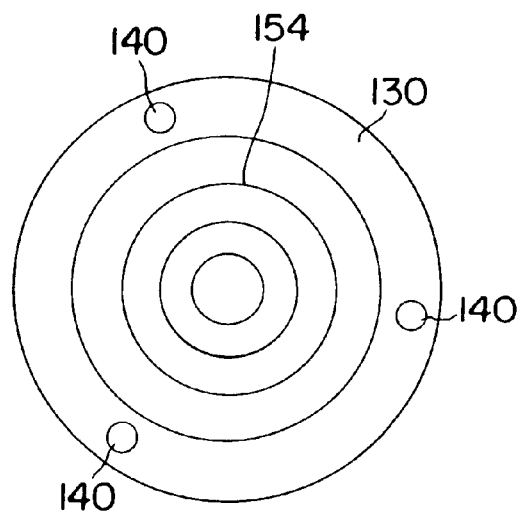
FIG. 7 is a top plan view of the scanning head of FIG. 6.

Casing 130 of scanning head 18 is illustrated in greater detail in FIGS. 6 and 7. A sectional view of the casing (FIG.

6) depicts the configuration of opening 132, which comprises a coupler portion 154 and a lens portion 156. Portion 154 houses coupler 134 (shown in FIG. 4) while portion 156 is used for mounting collimating lens 42 (shown in FIGS. 1 and 4). The path of radiant energy through the casing is restricted by a neck aperture 158 formed in casing 130. Inclined, through cavities 140, only one of which can be shown in the sectional view of FIG. 6, surround opening 132. The cavities contain optical fibers, such as fiber 54, and are equidistant from each other (FIG. 7). The fibers occupy the full length of cavities 140 such that the ends of the fibers are flush or only slightly recessed with respect to the endface of casing 130. The casing may be made of an opaque material e.g., aluminum, and is approximately 17.5 mm long. Neck aperture 158 restricts the diameter of the light path to approximately 2.0 mm.

Figure 8:
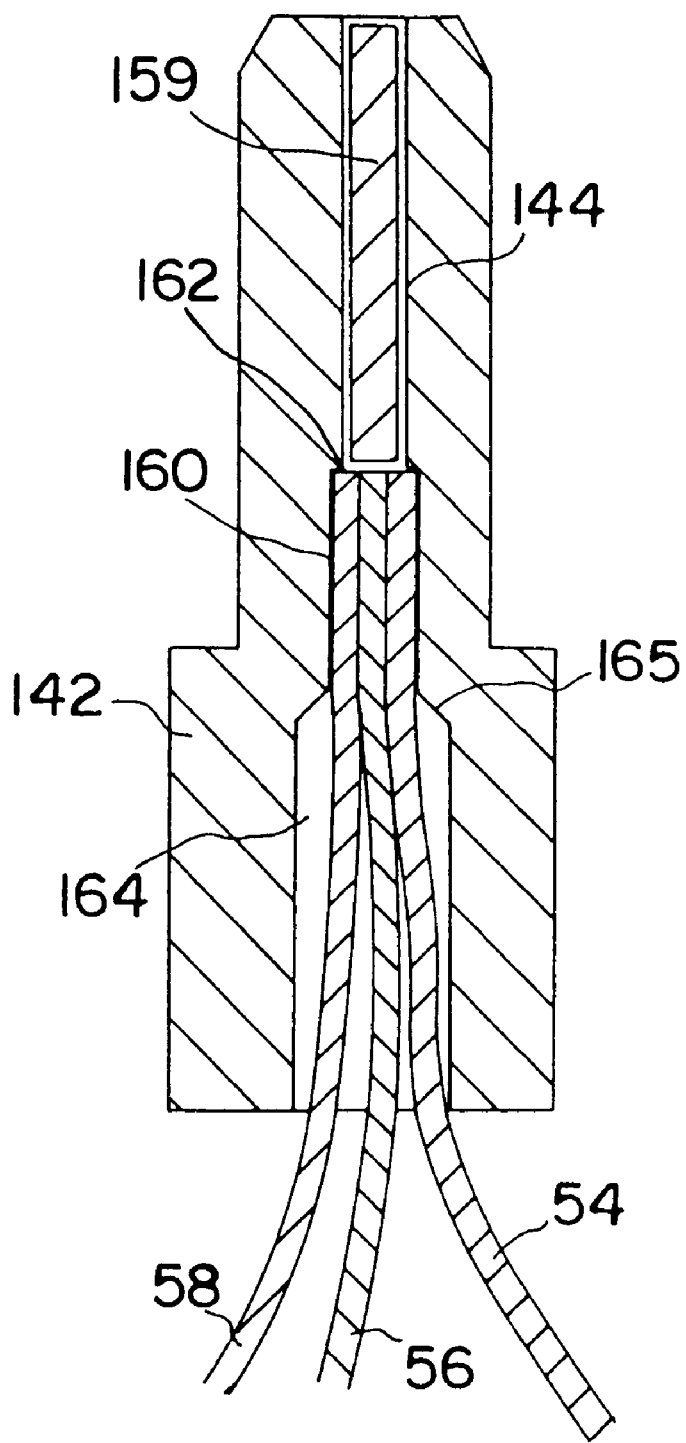
FIG. 8 is a sectional view of an optical-fiber integrator utilized by the photometer of FIG. 1.

The construction of optical-fiber integrator 142 is described in detail with reference to FIG. 8. Integrator 142 has a generally cylindrical shape and a centrally-disposed aperture 144 containing an optical fiber segment 159 that is secured inside the aperture, e.g., by an adhesive. Segment 159 completely fills aperture 144 such that one end of the segment is flush with the endface of integrator 142. The integrator also possesses a cylindrical bore 160 that accommodates the ends of optical fibers 54, 56, and 58, which are fixed inside the bore. Bore 160 has a slightly greater radius than aperture 144 and is joined therewith at a flange 162 so that fiber segment 159 is contiguous with fibers 54, 56, and 58. To maximize light transmission between fiber segment 159 and fibers 54, 56, and 58, the difference in the radial dimensions of aperture 144 and bore 160 is minimal. Thus, fibers 54, 56, and 58 each have a smaller diameter than segment 159 such that their combined cross-sectional area is approximately the same as that of segment 159. In turn, the diameter of segment 159 is the same as those of fibers 36, 38, 40, 60, and 62. To facilitate the insertion of the optical fibers into the integrator, an opening 164, which possesses a greater radius than the bore, is formed collinearly with the latter. Opening 164 has a countersink 165 for gradually guiding the ends of the optical fibers into bore 160. Integrator 142 may be made of an opaque material, e.g., aluminum. The integrator is about 25 mm long, aperture 144 is about 2.3 mm in diameter, and bore 160 has a diameter of approximately 2.3 mm.

Referring once again to FIG. 4, the coupling of the optical fibers is now further described. One end of fiber 40 is secured inside the bore of coupler 134 while the other end is routed inside coupler 152 via a lateral opening within sleeve 118. Similarly, the ends of fiber 38 are retained inside couplers 92 and 94. Fiber 60 and couplers 90 and 96 are arranged identically. A space of about 0.2 mm is provided between the juxtaposed faces of couplers 94 and 152 as well as between those of coupler 96 and integrator 142 for allowing member 14 of the movable arm to freely pivot with respect to member 16.

To link fibers 38 and 60 with the optical system described in the previous section of the specification, optical fibers 36 and 62, interfacing with the rest of the optical components, are routed into sleeve 110 via a lateral opening therein. The ends of these fibers are supported within couplers 107 and 109 anchored inside collars 106 and 108 such that the fibers 36 and 62 are collinear with fibers 38 and 60, respectively. A distance of approximately 0.2 mm separates the contiguous faces of couplers 90 and 107 as well as the faces of couplers 92 and 109. This permits member 16 to pivot freely with respect to housing 10. Fibers 38, 40, and 60 are approximately 20 cm long and 1.0 mm in diameter. Fibers 54, 56, and 58 each have a diameter of about 0.8 mm and a length of approximately 20 cm. In one embodiment of the invention, all optical fibers are made of quartz, thereby allowing transmission of ultraviolet light.

As noted above, the juxtaposed faces of the respective couplers (e.g., 94 and 152) are aligned such that the ends of their respective fibers are collinear and contiguous to maximize light transmission between the fibers. The alignment of the fibers is illustrated in FIG. 5A.

DYNAMIC OPTICAL-FIBER COUPLING PROVIDED BY MOVABLE ARM

The operation of dynamic optical-fiber couplings provided by arm 12 can now be outlined with reference to FIGS. 4 and 5A.

As table 20 positions scanning head 18 at various wells of the microplate, member 14 pivots on bearings 112 and 114 relative to member 16. In turn, member 16 pivots relative to housing 10 on bearings 102 and 104. Specifically, as member 14 rotates with respect to member 16, fibers 40, 54, 56, and 58 move together therewith without twisting or bending. Optical contact between fiber 40 and fiber 38 is maintained through the dynamic coupling provided by couplers 152 and 94 regardless of the angular relationship between members 14 and 16. Optical contact between fiber 60 and pick-up fibers 54, 56, and 58 is maintained in a similar manner with the use of coupler 96 and integrator 142. Moreover, the integrator allows the system to relay the optical signals of a plurality of fibers into a single fiber, thus providing a simple, yet extremely sensitive optical arrangement for performing fluorescence measurements.

Fibers 38 and 60 are also dynamically coupled with fibers 36 and 62, respectively, since couplers 90 and 92 rotate relative to housing 10 in respective bearings 102 and 104, whereas fibers 36 and 62 remain stationary in couplers 109 and 107, which are anchored to collars 106 and 108 of housing 10.

Thus, bending and twisting of optical fibers is eliminated, guaranteeing repeatability and consistency of measurements and preventing mechanical failure of fiber cores due to cyclical bending stresses. Moreover, since compliance of optical fibers does not affect the movement of scanning head 18, stiffer quartz fibers can now be employed to allow transmission of ultraviolet radiation, which may be useful in certain types of fluorescence measurements. Also, the absence of bending resistance in the fibers permits the positioning table to move the scanning head quickly enough to perform kinetic measurements.

Additionally, parallel beams 122 and 124 of member 14 allow the system to position lens 50 and photodetector 52 collinearly with respect to scanning head 18 so that absorbance measurements (typically done by passing radiant energy from fiber 40 to detector 52 through an analyte sample) can be performed together with fluorescence and luminescence assays. Furthermore, the scanning head orients the ends of optical fibers 54, 56, and 58 obliquely to its longitudinal axis to prevent the fibers from picking up optical noise from the edges of microplate wells during fluorescence and luminescence measurements. Fibers 54, 56, and 58 are designed to pick up (receive) fluorescence and luminescence emissions and fiber 40 is designated to provide the excitation light in the case of fluorescence. In this manner, fluorescence and luminescence measurements are taken above the microplate rather than through it.

MOVABLE ARM MODIFIED TO ACCOMMODATE ALTERNATIVE EMBODIMENT OF OPTICAL SYSTEM

Figure 3:
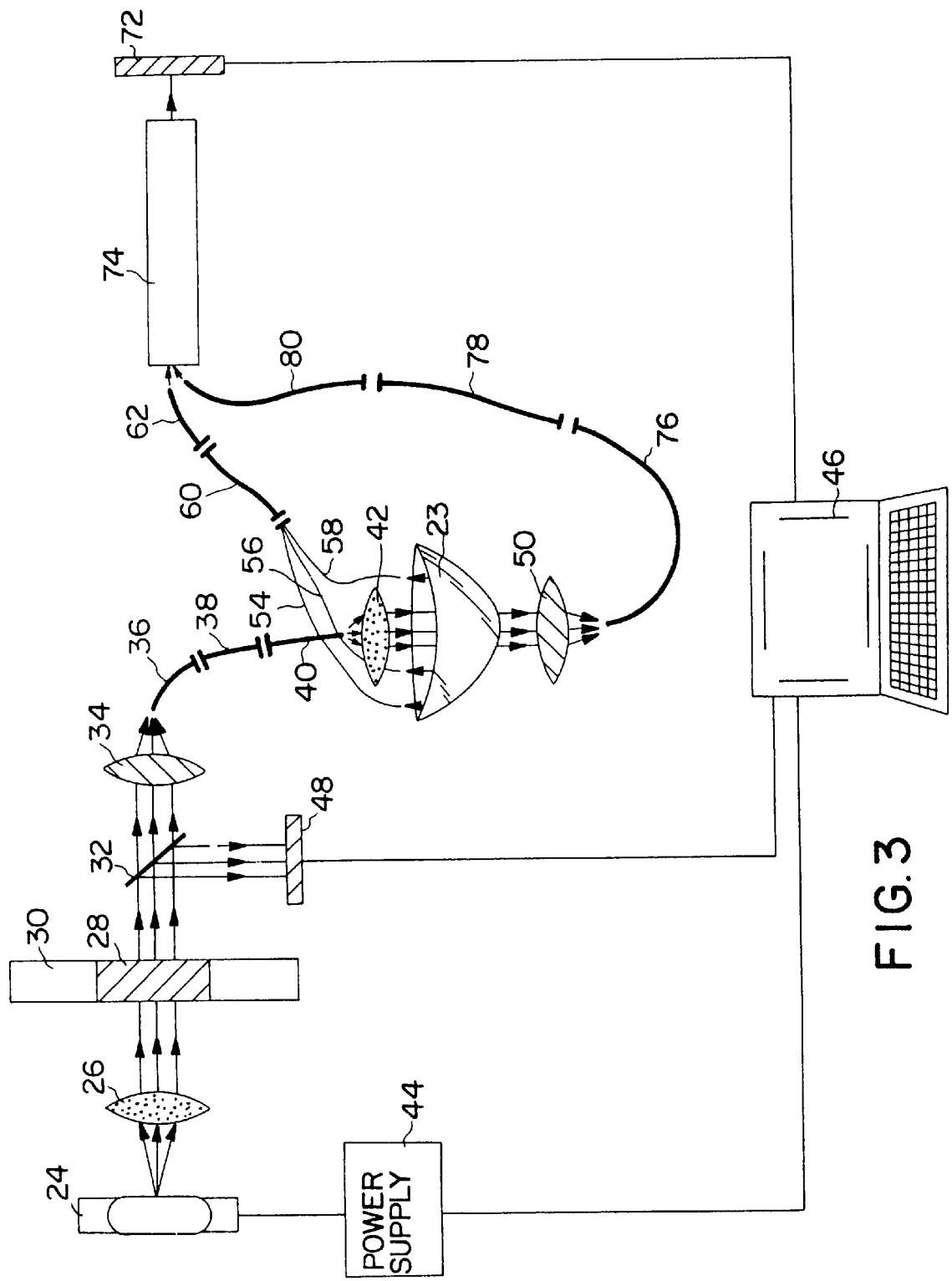
FIG. 3 is a schematic representation of an alternative embodiment of the optical system of FIG. 2.
Figure 9:
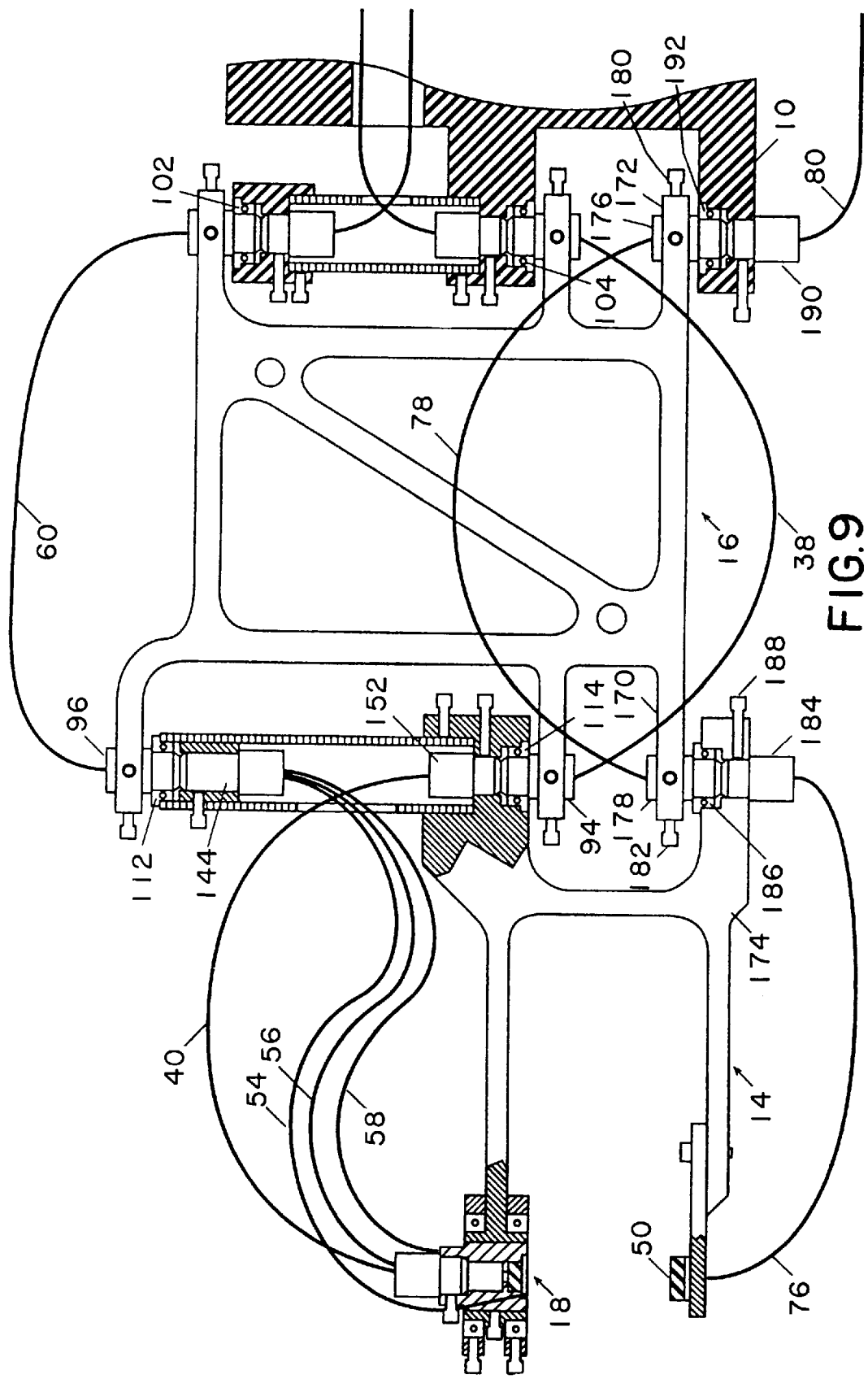
FIG. 9 is a side elevational view of the movable arm of FIG. 4 modified to accommodate the alternative embodiment of the optical system, shown in FIG. 3.

FIG. 9 shows a movable arm modified to accommodate the alternative embodiment of the optical system (illustrated in FIG. 3).

In order to provide an optical connection between the second scanning element, i.e., collimating lens 50, and light dispersing device 74 (FIG. 3), optical fibers 76 and 78 are attached to members 14 and 16, respectively. To accommodate these fibers, mounting protrusions 170 and 172 are added to member 16, whereas member 14 is formed with a second hinged portion 174. Protrusions 170 and 172 have openings for housing optical-fiber couplers 178 and 176, respectively. Couplers 178 and 176 are anchored within their respective openings with set screws 182 and 180 and accommodate ends of fiber 78 in their centrally-disposed through bores.

Hinged portion 174 possesses an opening for housing an optical coupler 184 and a bearing 186. Coupler 184 is positioned such that the through central bores of couplers 178 and 184 are collinear and a distance of about 0.2 mm separates their juxtaposed faces. Bearing 186 houses coupler 178 and, together with bearings 112 and 114, allows member 14 to pivot with respect to member 16. One end of fiber 76 is coupled to lens 50, while the other end is inserted into the bore of coupler 184, which is rigidly attached to member 14 with a set screw 188. As member 14 rotates with respect to member 16, integrator 144 and couplers 152 and 184 rotate together with member 14, whereas couplers 96, 94, and 178 are anchored to member 16 and remain stationary. Thus, member 14 can pivot with respect to member 16 without deforming fibers 76, 40, 54, 56, and 58.

To provide an optical interconnection between fibers 78 and 80, coupler 176 is mated with a coupler 190, which is rigidly attached to housing 10 and is collinear with coupler 190. A bearing 192, mounted in housing 10, supports coupler 176 and, together with bearings 102 and 104, allows member 16 to pivot with respect housing 10 without deforming fibers 38, 60, and 78.

Since lens 50 shares an optical axis with head 18, optically coupling the lens with light dispersing device 74 (FIG. 3) allows the photometer to analyze optical signals, resulting from the phenomenon of absorbance, over a broad range of wavelengths. Thus, a more comprehensive analysis of the analyte samples can be performed.

ALTERNATIVE EMBODIMENT OF THE MOVABLE ARM TO ACCOMMODATE REFLECTIVE SURFACES

Figure 11:
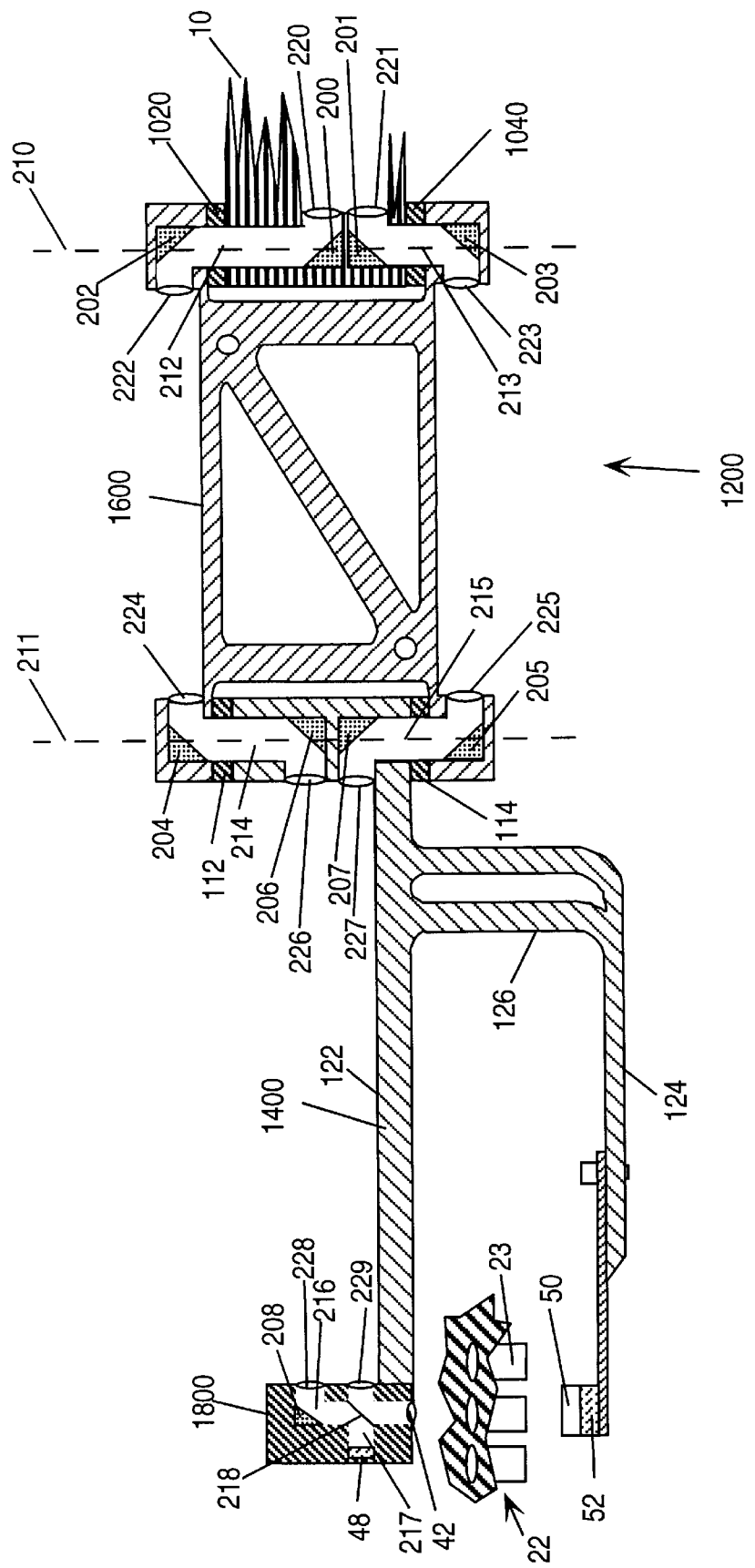
FIG. 11 is a side elevational view of an alternative embodiment of the movable arm of the photometer in which radiant energy is transferred from the optical system to the scanning head through the use of reflective surfaces.

FIG. 11 shows an alternative embodiment of the movable arm where reflective surfaces are used to route light between the optical system and the optical scanning head.

The movable arm 1200 is an articulated linkage having a C-shaped rigid elbow member 1400 and a rigid shoulder member 1600. The shoulder member 1600 is pivotally attached to a housing 10 by means of two ring bearings 1020 and 1040. This arrangement allows member 1600 to pivot with respect to housing 10 about an axis 210 defined by the pivotal centers of ring bearings 102 and 104. Similarly, ring bearings 112 and 114 allow shoulder member 1600 to pivotally support C-shaped elbow member 1400. This arrangement allows member 1400 to pivot with respect to member 1600 about an axis 211 defined by the pivotal centers of ring bearings 112 and 114. Bearings 102, 104, 112 and 114 have openings through their respective pivotal centers such that routed radiant energy can pass therethrough.

Elbow member 1400 further includes parallel beams 122 and 124, integrally connected by a shank 126. Beam 122 is attached to a scanning head 1800 whereas beam 124 bears the second scanning element comprising a lens 50 and a photodetector 52 which is collinear with the scanning head.

Scanning head 1800 includes a cavity 216 through which radiant energy is routed. Cavity 216 houses a reflective surface 208 at one end, a lens 42 at the other end, and a beam splitter 218 disposed therebetween. Scanning head 1800 further includes an opening 228 which enables reflective surface 208 to be optically coupled to the optical system such that radiant energy from the optical system (e.g. the optical system in housing 10) may be directed upon the reflective surface 208. Scanning head 1800 further comprises a cavity 217 through which radiant energy is routed. Cavity 217 houses a photodetector 48 at one end, an opening 229 at the other, and beam splitter 218 disposed therebetween. Cavities 216 and 217 are aligned perpendicular to each other, but may be disposed at various angles within scanning head 1800 relative to elbow member 1400. Cavities 216 and 217 may also be filled with any media through which radiant energy may be transmitted. Similarly, optical couplings 212, 213, 214, and 215 may be filled with any media through which radiant energy may be transmitted.

The light-delivering assembly described in FIGS. 1 and 2 is modified in FIG. 11. In order to transmit radiant energy from light source 24 (shown in FIG. 1) to the analyte sample in well 23 of microplate 22, optical fibers 36, 38 and 40 of the light-delivering system of FIG. 1 are replaced in FIG. 11 by optical input couplings 212 and 214 and reflective surfaces 200, 202, 204, 206 and 208. Reflective surfaces 200, 202, 204, 206 and 208 are typically mirrors, but can be composed of any material capable of reflecting radiant energy.

Optical input coupling 212, disposed along axis 210, is comprised of reflective surfaces 200 and 202, and openings 220 and 222 to allow for the routing of radiant energy. Housing reflective surface 200 and shoulder reflective surface 202 are mounted to the housing and shoulder members respectively and are disposed along axis 210. Radiant energy (e.g. an excitation light for fluorescence spectroscopy) is transmitted through opening 220, reflected from reflective surface 200 to reflective surface 202, routed through opening 222 to reflective surface 204 on shoulder member 1600; this routing of radiant energy from reflective surface 202 to reflective surface 204 optically interconnects optical input coupling 214 to optical input coupling 212.

Optical input coupling 214, disposed along axis 211, is comprised of reflective surfaces 204 and 206, and openings 224 and 226 to allow for the passage of radiant energy. Shoulder reflective surface 204 and elbow reflective surface 206 are mounted to the shoulder and elbow members respectively and are disposed along axis 211. Radiant energy exiting opening 222 of the optical input coupling 212 is transmitted through opening 224, reflected from reflective surface 204 to reflective surface 206, routed through opening 226 to reflective surface 208 in scanning head 1800; this routing of radiant energy from reflective surface 206 to reflective surface 208 optically interconnects scanning head 18 to optical input coupling 214. Radiant energy exiting opening 226 is routed through opening 228 of scanning head 1800, reflected off of reflective surface 208 and split by beam splitter 218. Thus, radiant energy is transmitted towards the analyte sample in microplate 22 and towards photodetector 48 of the light-gathering assembly.

The light-gathering assembly for absorbance measurements comprises a reference-signal photodetector 48 and a beam splitter 218 disposed within scanning head 1800, a focusing lens 50, and a second scanning element for collecting light transmitted through microplate 22, e.g., a photodetector 52. Radiant energy routed from reflective surface 208 is split by beam splitter 218 and routed to lens 42 and photodector 48. Photodetectors 48 and 52, which convert electromagnetic radiation into electric current, may be implemented as photovoltaic cells. After being converted to a digital format by an analog-to-digital converter (not shown), the outputs of photodetectors 48 and 52 are analyzed by microcomputer 46 (shown in FIG. 1).

The light-gathering assembly for fluorescence and luminescence measurements of the optical system described in FIGS. 1 and 2 is modified in FIG. 11. The optical pick-up fibers 54, 56 and 58, the light-transmitting fiber 60, and the optical fiber 62 of the light-delivery system of FIG. 1 are replaced in FIG. 11 by the beam splitter 218, optical pick-up couplings 215 and 213, and reflective surfaces 207, 205, 203, and 201. Reflective surfaces 207, 205, 203, and 201 are typically mirrors, but can be composed of any material capable of reflecting radiant energy.

In fluorescence and luminescence measurements, fluorescent (or luminescent) radiant energy is picked-up and routed through cavity 217 of scanning head 1800. Such radiant energy is reflected off beam splitter 218 through opening 229 to reflector 207 in optical pick-up coupling 215.

Optical pick-up coupling 215 is comprised of reflective surfaces 207 and 205, and openings 227 and 225 to allow for the passage of fluorescent (or luminescent) radiant energy. Shoulder reflective surface 205 and elbow reflective surface 207 are mounted to the shoulder and elbow members respectively and are disposed along axis 211. Radiant energy from opening 229 of scanning head 1800 is transmitted through opening 227, reflected from reflective surface 207 to reflective surface 205, routed through opening 225 to reflective surface 203, and consequently optical pick-up coupling 215 is optically interconnected to optical pick-up coupling 213.

Optical pick-up coupling 213 is comprised of reflective surfaces 203 and 201, and openings 223 and 221. Shoulder reflective surface 203 and housing reflective surface 201 are mounted to the shoulder and housing members respectively. Radiant energy from optical input coupling 215 is transmitted through opening 223, reflected off reflective surface 203 to reflective surface 201, routed through opening 221, and optically interconnected to the optical system (e.g. an optical system within housing 10).

Through the arrangement of the light-gathering and light-delivering assemblies illustrated in FIG. 11, shoulder member 1600 and elbow member 1400 are able to supportingly route light-transmitting paths such that the transmitted light remains at a constant intensity along the paths regardless of the pivotal movement of the shoulder member 1600 with respect to housing 10, or the pivotal movement of elbow member 1400 with respect to shoulder member 1600.

As shown in FIG. 11, the reflective surfaces 200 and 201 are fixedly mounted to housing 10, reflective surfaces 202, 203, 204 and 205 are fixedly mounted to the shoulder member 1600, reflective surfaces 206 and 207 are fixedly mounted to the elbow member 1400, and reflective surface 208 is fixedly mounted to scanning head 1800. However, the reflective surfaces may be mounted such that they are capable of being rotated to face in any direction to route radiant energy at a constant intensity between the optical system and scanning head 1800. The rotation and position of the reflective surfaces may be controlled and coordinated by microcomputer 46 (shown in FIG. 1).

ALTERNATIVE EMBODIMENT OF THE MOVABLE ARM TO ACCOMMODATE REFLECTIVE SURFACES AND OPTICAL FIBERS

Figure 12:
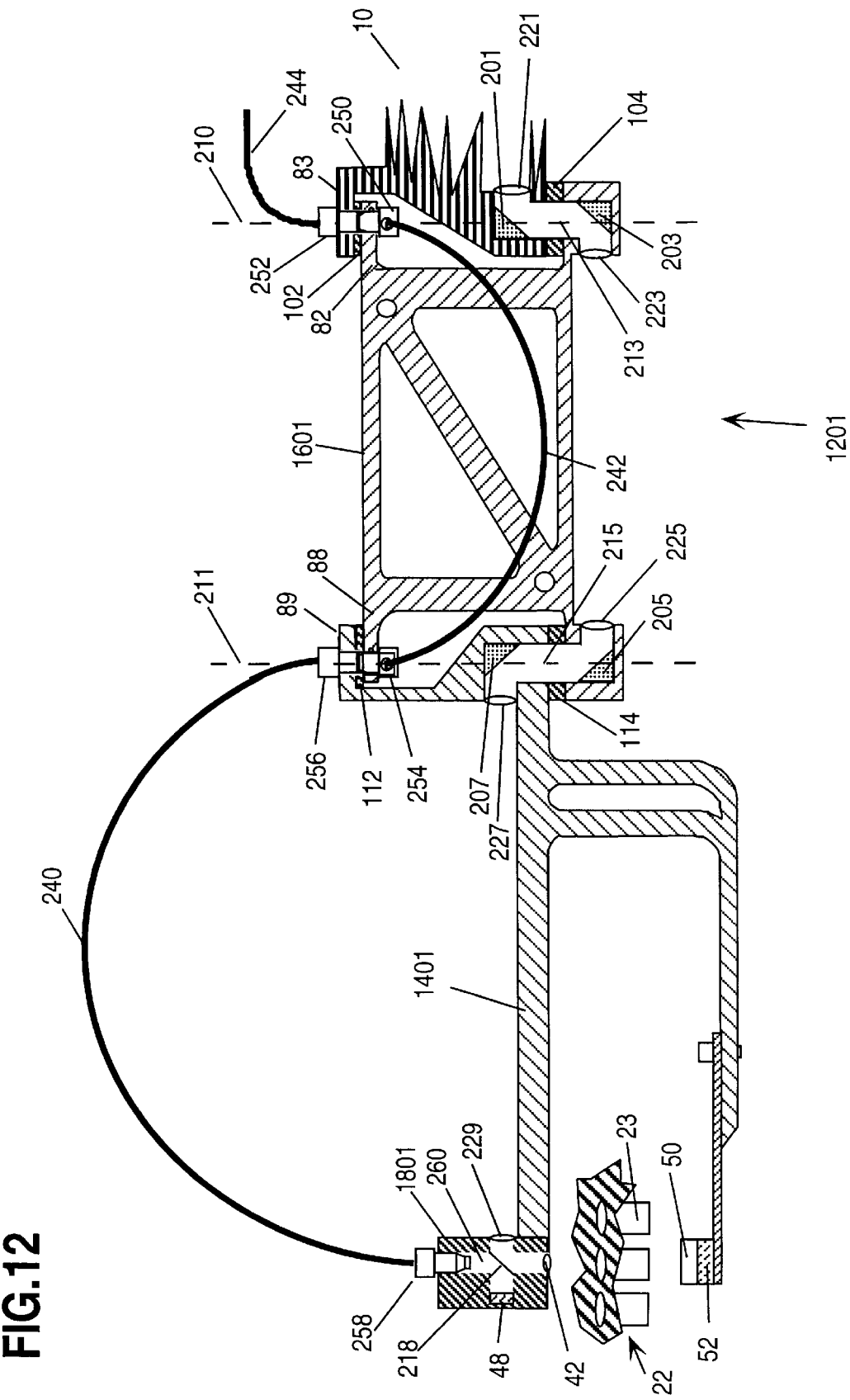
FIG. 12 is a side elevational view of an alternative embodiment of the movable arm of the photometer in which radiant energy is transferred to and from the scanning head through a combination of reflective surfaces and optical fibers.

FIG. 12 shows an alternative embodiment of the movable arm illustrated in FIG. 11, in which both optical fibers and reflective surfaces are utilized in transmitting radiant energy between the optical system and the scanning head.

In FIG. 12, the light-delivering assembly of FIG. 11 is replaced by an assembly similar to that illustrated in FIG. 4. The light-delivering assembly of FIG. 12 employs optical fibers 240, 242 and 244 together with optical-fiber couplers 250, 252, 254, 256 and 258. The optical-fiber couplers are the same as shown in FIG. 5.

In order to provide an optical connection between scanning head 1801 and the optical system, optical fibers 240, 242, and 244 are employed. Optical fiber 240 is fixedly attached to scanning head 1801 and elbow member 1401, optical fiber 242 is fixedly attached to shoulder member 1601, and optical fiber 244 is fixedly attached to housing 10 and optically coupled to the optical system, such as an optical system within housing 10.

To accommodate optical fiber 240, elbow member 1401 includes a mounting protrusion 89 and scanning head 1801 includes a through bore 260. Through bore 260 houses optical-fiber coupler 258 at one end, lens 42 at the other, and beam splitter 218 disposed therebetween. Mounting protrusion 89 has an opening for housing optical-fiber coupler 256. Couplers 256 and 258 have centrally-disposed through bores to accommodate the ends of fiber 240.

To accommodate optical fiber 242, shoulder member 1601 includes mounting protrusions 88 and 82. Protrusions 88 and 82 have openings for housing optical-fiber couplers 254 and 250 respectively. Couplers 254 and 250 have centrally-disposed through bores to accommodate the ends of fiber 242. Coupler 254 is positioned such that the through central bores of coupler 254 and coupler 256 are arranged collinearly with axis 211, and their juxtaposed faces are positioned at a distance of about 0.2 mm from each other.

To accommodate optical fiber 244, housing member 10 includes a mounting protrusion 83. Protrusion 83 has an opening for housing optical-fiber coupler 252. Coupler 252 has a centrally-disposed through bore to accommodate the end of fiber 244. Coupler 250, rigidly mounted to protrusion 82, and coupler 252, rigidly mounted to protrusion 83, are positioned such that the through central bores of coupler 250 and coupler 252 are arranged collinear with axis 210, and their juxtaposed faces are positioned at a distance of about 0.2 mm from each other.

Ring bearings 112 and 114 allow shoulder member 1601 to pivot with respect to elbow member 1401 about axis 211. One end of fiber 240 is inserted into the bore of coupler 258, which is rigidly attached to scanning head 1801, while the other end of fiber 240 is inserted into the bore of coupler 256, which is rigidly attached to protrusion 89. As elbow member 1401 rotates with respect to shoulder member 1601, coupler 256 and elbow reflective surface 207 rotate together with elbow member 1401, whereas coupler 254 and shoulder reflective surface 205, which are fixedly attached to shoulder member 1601, remain stationary. Thus, elbow member 1401 can pivot with respect to shoulder member 1601 without deforming fiber 240.

Similarly, ring bearings 102 and 104 allow shoulder member 1601 to pivot with respect to housing 10 about axis 210. As shoulder member 1601 rotates with respect to housing 10, coupler 250 and shoulder reflective surface 203 rotate together with shoulder member 1601, whereas coupler 252 and housing reflective surface 201, which are fixedly attached to housing 10, remain stationary. Thus, shoulder member 1601 can pivot with respect to housing 10 without deforming fiber 242.

The light-gathering assembly illustrated in FIG. 12 for absorbance, fluorescence and luminescence measurements remains unchanged from FIG. 11. The light-gathering assembly for absorbance measurements typically comprises a reference-signal photodetector 48, beam splitter 218, focusing lens 50 and photodector 52. Radiant energy exiting from optical-fiber coupler 258, is split by beam splitter 218 and routed to lens 42 and photodector 48. Photodectors 48 and 52, which convert electromagnetic radiation into electric current, may be implemented as photovoltaic cells. After being converted to a digital format by an analog-to-digital converter (not shown), the outputs of photodetectors 48 and 52 are analyzed by microcomputer 46 (shown in FIG. 1). For fluorescence or luminance measurements, the light gatherng assembly includes beam splitter 218 which reflects fluorescent or luminescent emissions to reflective surface 207 and then to reflective surface 205 and then to reflective surface 203 and then to reflective surface 201.

ALTERNATIVE EMBODIMENT OF THE MOVABLE ARM TO ACCOMMODATE OPTICAL FIBERS AND ONE REFLECTIVE SURFACE

Figure 13:
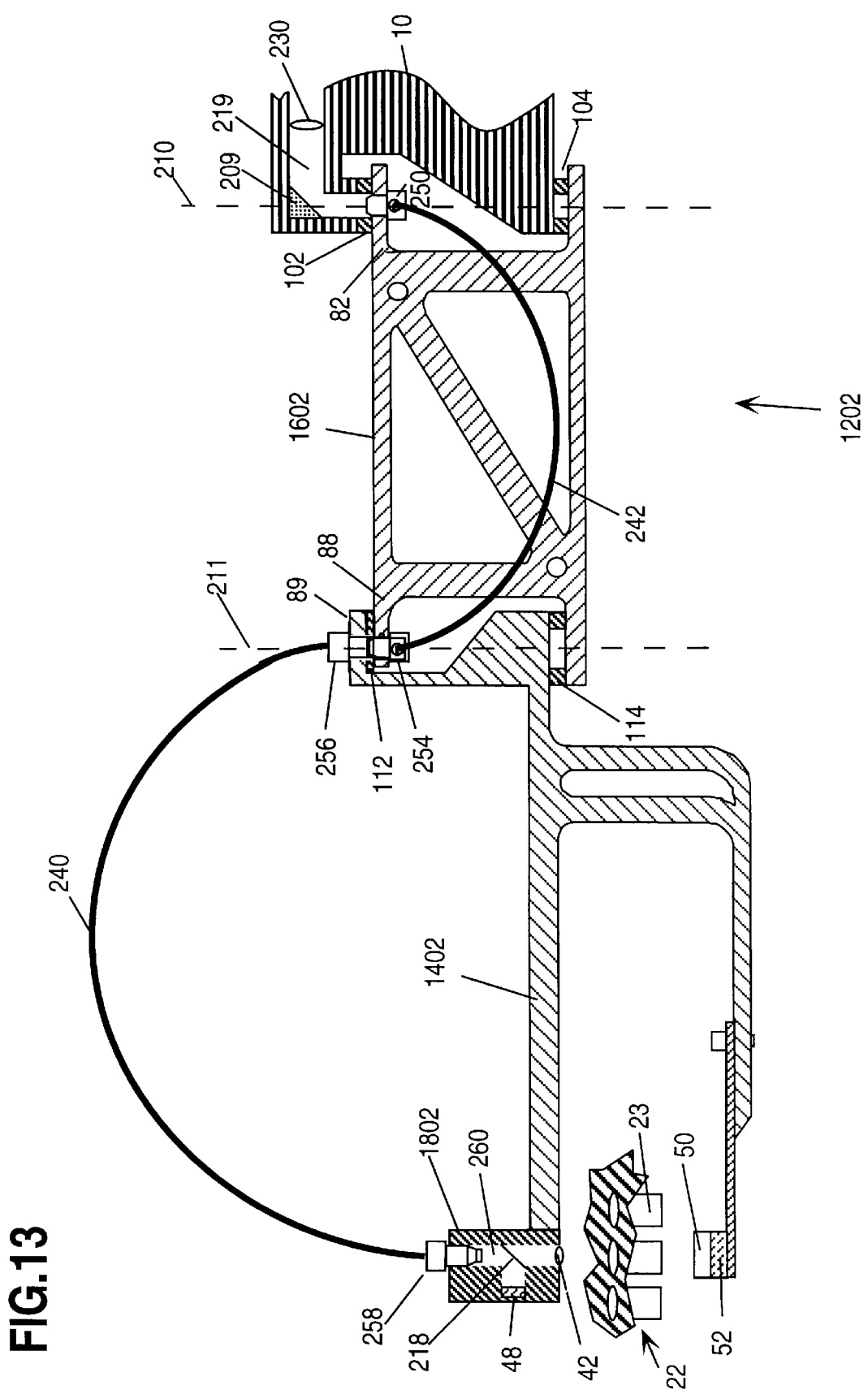
FIG. 13 is a side elevational view of an alternative embodiment of the movable arm of the photometer in which one reflective surface is utilized in conjunction with optical fib to transfer radiant energy to the scanning head.

FIG. 13 shows an alternative embodiment of the movable arm illustrated in FIG. 12, in which optical fibers and one reflective surface are utilized in the light-delivering assembly. The light gathering assembly comprises a photodector 52, lens 50 and photodetector 48 with beam splitter 218.

As in FIG. 12, the light-delivering assembly includes optical fibers 242 and 240, and optical-fiber couplers 250, 254, 256 and 258. However, optical fiber 244 and optical-fiber coupler 252 in FIG. 12 are replaced in FIG. 13 by optical input coupling 219 which optically interconnects the optical system (e.g. an optical system in housing 10) to optical-fiber coupler 250.

Optical input coupling 219 is arranged collinearly with axis 210 and includes opening 230 and housing reflective surface 209. Radiant energy is routed through opening 230, reflected off surface 209, and optically coupled to fiber 242 via coupler 250. Ring bearings 102 and 104 allow shoulder member 1602 to pivot with respect to housing 10. Coupler 250, fixedly attached to shoulder member 1602, rotates with shoulder member 1602 as shoulder member 1602 pivots with respect to housing 10 about axis 210. Thus, shoulder member 1602 can pivot with respect to housing 10 without deforming fiber 242. Similarly, ring bearings 112 and 114 allow elbow member 1402 to pivot with respect to shoulder member 1602 about axis 211 without deforming fiber 240.

The light-gathering assembly illustrated in FIG. 13 is typically used for absorbance measurements and remains unchanged from FIG. 12.

OPERATION OF PHOTOMETER

Figure 10:
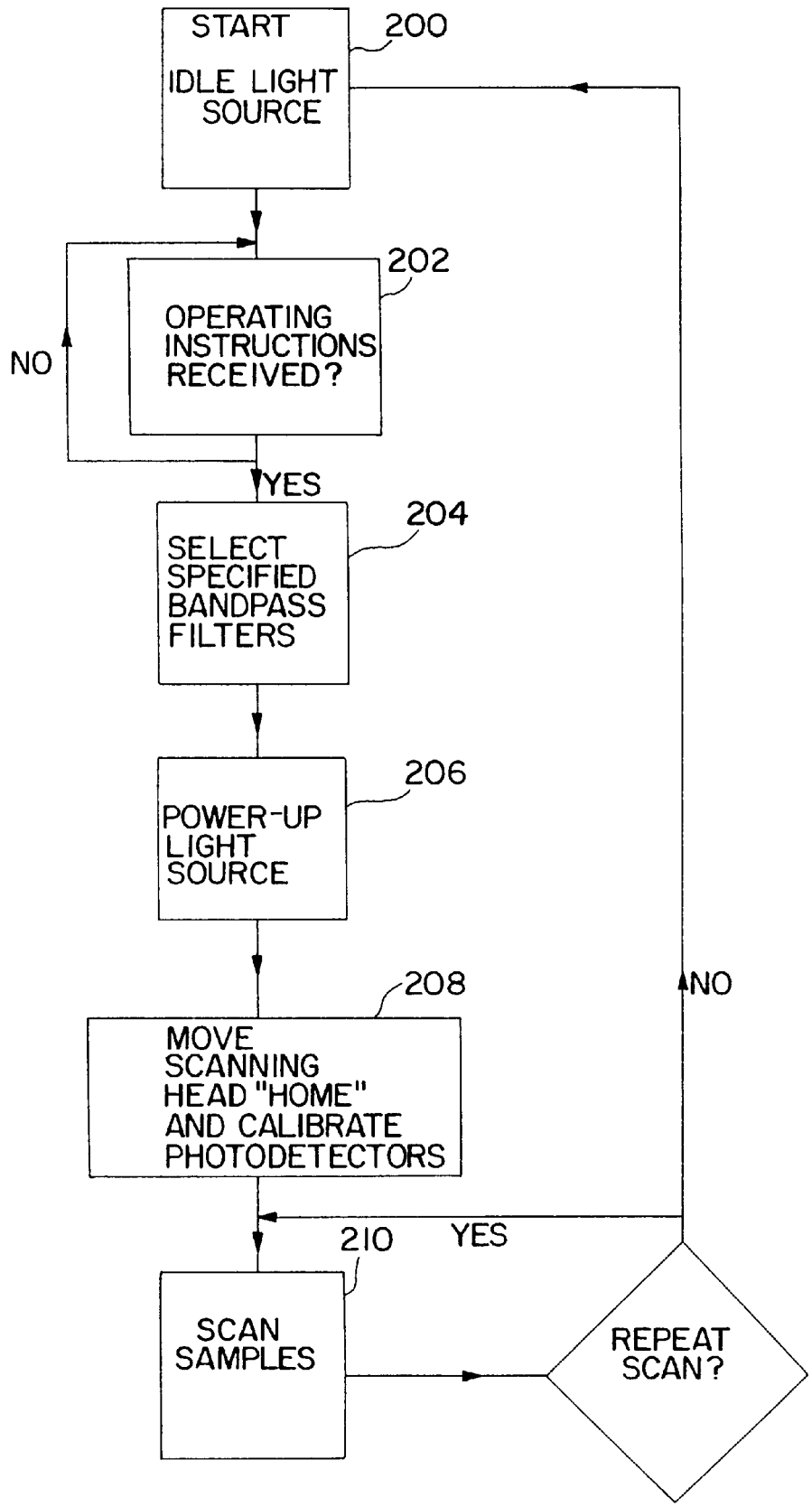
FIG. 10 is a block diagram illustrating the operation of the photometer of FIG. 1.

Operation of the photometer is described in reference to the general steps outlined in FIG. 10 and the apparatus shown in FIG. 1.

As the photometer is initially energized (step 200), microcomputer 46 instructs power supply 44 to maintain light-source 24 in idle mode by applying power of approximately 30 Watts to the light-source.

The microcomputer is then provided with a set of operating instructions (step 202). These contain information regarding specific measurement parameters, e.g., type of scan (absorbance, fluorescence, or luminescence measured individually or simultaneously), number of times to repeat the scanning cycle, various geometries of microplate-well arrays, filter positions, duration of scanning cycle, etc.

In accordance with the instructions received in step 202, the microcomputer selects appropriate bandpass filters 28 and 66 by rotating filter wheels 30 and 68, respectively (step 204). After the selection of the filters is completed, the microcomputer instructs the power supply to increase power applied to the light source to approximately 75 Watts (step 206).

After the light source has been powered up, the microcomputer directs positioning table 20 to move head 18 to a predetermined "home" position (step 208), where the light path between head 18 and photodetector 52 is unobstructed by microplate 22. Calibration of photodetectors 48 and 52 is then performed for absorbance measurements.

Following photodetector calibration, microcomputer 46 directs table 20 to move head 18 such that samples located in specified wells 23 of microplate 22 are scanned (step 210). During a scan, signals of photodetector 72 and/or photodetectors 48 and 52 are processed by the microcomputer to measure one or more of absorbance, fluorescence, and luminescence of the analyte samples.

Depending on the instructions received during step 202, the microprocessor either repeats the scan (step 210) or switches the light source to idle mode (step 200).

Because of the optical coupling provided by movable arm 12, the optical energy path routed along the reflective surfaces remains constant, so that measurements produced during a scan are consistent from sample to sample. Moreover, measurements from one scan to another are fully repeatable. Additionally, since cyclical bending of fibers does not occur, the reflective surfaces alone, or in conjunction with quartz optical fibers can be used to perform spectroscopic analyses in the ultraviolet region of the spectrum.

Thus, it has been shown that we have provided a multi-functional photometer which measures absorbance, fluorescence, and luminescence of a sample; which provides repeatable measurements and produces consistent readings between different test sites; which eliminates recurring bending of optical fibers and mechanical failure thereof; which utilizes optical radiation ranging from the ultraviolet to the infrared spectrum; which is able to carry out kinetic measurements; which can accommodate microplates with different well configurations; and which is relatively simple and inexpensive to manufacture.

Although the multi-functional photometer has been shown and described in the form of specific embodiments, its configurations and materials are given only as examples, and many other modifications of the apparatus are possible. For example, the photodetectors utilized in the optical system may be executed as photoemissive tubes, photomultiplier tubes, photodiodes, etc. A prism, as well as a filter, may be used to disperse light instead of a diffraction grating. Light sources, such as xenon flash lamps, tungsten-halogen lamps, lasers and mercury vapor lamps may be employed with the optical system of the apparatus. Liquid-filled optical fibers may replace glass and plastic fibers. Optical-fiber couplers and integrator may be made of a plurality of opaque materials and may have different configurations. For instance, the optical fiber integrator may accommodate a multiplicity of fibers. Moreover, a coupling with two integrators may be used to optically interconnect two pluralities of fibers. The reflective surfaces may be mirrors or any material capable of reflecting radiant energy. Additionally, an axial positioning scale may take place of the Cartesian-coordinate positioning table. Instead of microplate wells, analyte samples may be placed in membranes or gels. It will also be appreciated that the photometer may be operated without computer control, as in the case of numerous prior-art photometers that do not require such control.

Therefore, the scope of the invention should be determined, not by the examples given, but by the appended claims and their equivalents.

What we claim is:

1. A photometer utilizing light-transmitting paths for analyzing optical properties of at least one analyte sample, said photometer comprising:
   an optical system; and
   a scanner for reading said at least one analyte sample, said scanner being optically coupled with said optical system by said light-transmitting paths including at least one reflective surface, said light-transmitting paths having fixed individual shapes, said scanner including a movable arm supportingly routing said light-transmitting paths and maintaining said fixed individual shapes of said light-transmitting paths as said scanner scans said at least one analyte sample and wherein said light-transmitting paths and said at least one reflective surface move in space as said scanner scans.

2. The photometer of claim 1 further includes a logic device which controls said scanner and said optical system.

3. The photometer of claim 2 wherein said logic device comprises a computer.

4. The photometer of claim 1 wherein said scanner further comprises:
   a housing capable of supporting a structure for holding said at least one analyte sample;
   a positioning device; and
   a first optical scanning element coupled to said positioning device, said first optical scanning element optically coupled with said optical system by a first arrangement of said light-transmitting paths, said positioning device capable of imparting scanning movements to said first optical scanning element in order to scan said at least one analyte sample.

5. The photometer of claim 4 wherein said positioning device is a Cartesian-coordinate positioning table controlled by a computer.

6. The photometer of claim 4 wherein said movable arm comprises:
   a first rigid member pivotally attached to said housing at a first axis;
   a second rigid member pivotally attached to said first rigid member at a second axis and having a first beam, said first optical scanning element attached to said first beam;
   couplings for optically and pivotally interconnecting said light-transmitting paths, said couplings disposed along said first and said second axes on said first and said second rigid members.

7. The photometer of claim 6 wherein said second rigid member further includes a second beam, said scanner further comprising a second optical scanning element coupled to said second beam, said first and said second optical scanning elements sharing an optical axis.

8. The photometer of claim 7 wherein said second optical scanning element comprises a photodetector.

9. The photometer of claim 7 wherein said second optical scanning element is optically coupled to a light-dispersing device by second arrangement of said light-transmitting paths having fixed individual shapes, said second arrangement of said light-transmitting paths supported by said movable arm and optically-interconnected by said couplings.

10. The photometer of claim 9 wherein said light-dispersing device comprises a beam splitter.

11. The photometer of claim 9 wherein said second optical scanning element comprises a lens.

12. The photometer of claim 6 wherein said couplings include pairs of reflective surfaces being collinear and optically interconnecting said light-transmitting paths.

13. The photometer of claim 6 wherein said couplings include conduit couplers arranged in pairs and reflective surfaces arranged in pairs, each of said conduit couplers having a through aperture, each of said through apertures housing an end of one of said light-transmitting paths, the through apertures of each of said pairs of conduit couplers being collinear and optically interconnecting the ends of the light-transmitting paths inserted therein, each of said reflective surfaces being collinear and optically interconnecting said light-transmitting paths.

14. The photometer of claim 6 wherein said couplings include conduit couplers arranged in pairs and at least one coupling comprising one of said conduit couplers paired with a reflective surface, each of said conduit couplers having a through aperture, each of said through apertures housing an end of one of said light-transmitting paths, the through apertures of each of said pairs of conduit couplers being collinear and optically interconnecting the ends of the light-transmitting paths inserted therein, wherein said reflective surface and said through aperture being collinear and optically interconnecting said light-transmitting paths.

15. The photometer of claim 4 wherein said first optical scanning element includes a body having a cavity wherein said cavity houses at least one of said light-transmitting paths.

16. The photometer of claim 12 said cavity further houses a lens.

17. The photometer of claim 1 wherein said optical system further includes:
   a light source; and
   a power supply for energizing said light source, said power supply being controlled by a computer.

18. The photometer of claim 17 wherein said light-source is a xenon arc lamp.

19. The photometer of claim 17 wherein said power supply is a direct-current power supply.

20. The photometer of claim 17 wherein said light-source is a laser.

21. The photometer of claim 1 wherein said optical properties are at least one of absorbance, fluorescence, and luminescence.

22. The photometer of claim 1 wherein said light-transmitting paths further include at least one optical fiber optically coupled to said at least one reflective surface of said light-transmitting paths.

23. The photometer of claim 1 wherein said light-transmitting paths further includes a plurality of reflective surfaces.

24. A photometer for measuring optical properties of at least one analyte sample, said photometer comprising:
   an optical system having a plurality of lenses; and
   a scanning mechanism comprising:
      a housing capable of supporting a structure for holding said at least one analyte sample;
      a positioning device;
      a first optical scanning element coupled to said positioning device, said first optical scanning element being optically coupled to said optical system by light-transmitting paths including at least one reflective surface, said light-transmitting paths having fixed individual shapes, said positioning device capable of imparting scanning movements to said first optical scanning element in order to scan said at least one analyte sample; and a movable linkage coupled to said first optical scanning element, said movable linkage supportingly routing said light-transmitting paths and maintaining said fixed individual shapes of said light-transmitting paths as said scanning mechanism scans and wherein said light-transmitting paths and said at least one reflective surface move in space as said scanning mechanism scans.

25. The photometer of claim 24 further including a microprocessor for controlling said positioning device and for monitoring said optical system.

26. The photometer of claim 24 wherein said optical system further includes a light source energized by a computer-controlled power supply.

27. The photometer of claim 26 wherein said light source is a xenon arc lamp.

28. The photometer of claim 26 wherein said light source is a laser.

29. The photometer of claim 26 wherein said computer-controlled power supply is a direct-current power supply.

30. The photometer of claim 24 wherein said light-transmitting paths further include at least one optical fiber optically coupled to said at least one reflective surface of said light-transmitting paths.

31. The photometer of claim 24 wherein said movable linkage comprises:

a rigid shoulder member pivotally attached to said housing at a first axis; and a rigid elbow member pivotally attached to said rigid shoulder member at a second axis and having a first beam, said first optical scanning element attached to said first beam.

32. The photometer of claim 31 wherein said light-transmitting paths further include:

a first optical input coupling arranged collinearly with said first axis, said first optical input coupling optically coupled to said first optical scanning element by a second optical input coupling, said second optical input coupling arranged collinearly with said second axis, said first optical input coupling optically coupled to said optical system; and a first optical pick-up coupling arranged collinearly with said first axis, said first optical pick-up coupling optically coupled to said first optical scanning element by a second optical pick-up coupling, said second optical pick-up coupling arranged collinearly with said second axis, said first optical pick-up coupling optically coupled to said optical system.

33. The photometer of claim 32 where in said rigid elbow member further includes a second beam bearing a second optical scanning element, said first and second optical scanning elements sharing an optical axis.

34. The photometer of claim 33 wherein said second optical scanning element comprises a photodetector.

35. The photometer of claim 33 wherein said second optical scanning element is optically coupled to a light dispersing device.

36. The photometer of claim 33 wherein said second optical scanning element comprises a lens.

37. The photometer of claim 24 wherein said first optical scanning element further includes:

a body having a symmetry axis;

a cavity disposed within said body;

a scanning element reflective surface disposed within said cavity, said scanning element reflective surface arranged collinearly with said symmetry axis; and a lens disposed within said cavity, said lens being collinear with said symmetry axis.

38. The photometer of claim 37 wherein the first optical scanning element further includes:

a photodetector disposed within said cavity; and a beam splitter disposed within said cavity, said beam splitter arranged collinearly with said symmetry axis and angularly disposed between said scanning element reflective surface and said lens, said beam splitter optically coupling said photodetector to said scanning element reflective surface.

39. The photometer of claim 32 wherein:

said first optical input coupling comprises a first housing reflective surface and a first shoulder reflective surface, said first housing reflective surface optically connecting said first shoulder reflective surface to said optical system by providing a light path therebetween;

said first optical pick-up coupling comprises a second housing reflective surface and a second shoulder reflective surface; said second housing reflective surface optically connecting said second shoulder reflective surface to said optical system by providing a light path therebetween;

said second optical input coupling comprises a third shoulder reflective surface and a first elbow reflective surface; said third shoulder reflective surface optically connecting said first shoulder reflective surface to said first elbow reflective surface by providing a light path therebetween, said first elbow reflective surface optically connecting said third shoulder reflective surface to said scanning element reflective surface of said first optical scanning element by providing a light path therebetween;

said second optical pick-up coupling comprises a fourth shoulder reflective surface and a second elbow reflective surface; said fourth shoulder reflective surface optically connecting said second shoulder reflective surface to said second elbow reflective surface by providing a light path therebetween, said second elbow reflective surface optically connecting said fourth shoulder reflective surface to said beam splitter of said first optical scanning element by providing a light path therebetween.

40. The photometer of claim 24 wherein said optical properties are at least one of absorbance, fluorescence, and luminescence.

41. The photometer of claim 24 wherein said positioning device comprises a Cartesian-coordinate positioning table.

* * * * *